US011250950B1

(12) United States Patent
Miller et al.

(10) Patent No.: US 11,250,950 B1
(45) Date of Patent: Feb. 15, 2022

(54) MACHINE-LEARNING BASED QUERY CONSTRUCTION AND PATTERN IDENTIFICATION FOR AMYOTROPHIC LATERAL SCLEROSIS

(71) Applicant: HVH Precision Analytics LLC, King of Prussia, PA (US)

(72) Inventors: Chris Miller, Conshohocken, PA (US); Manjula Kasoji, Gaithersburg, MD (US); Oodaye Shukla, Chesterbrook, PA (US); Cody Garges, Chalfont, PA (US); Tara Grabowsky, Bryn Mawr, PA (US); Ron Payne, Fort Washington, PA (US)

(73) Assignee: HVH PRECISION ANALYTICS LLC, King of Prussia, PA (US)

( * ) Notice: Subject to any disclaimer, the term of this patent is extended or adjusted under 35 U.S.C. 154(b) by 632 days.

(21) Appl. No.: 15/719,047

(22) Filed: Sep. 28, 2017

Related U.S. Application Data

(60) Provisional application No. 62/404,338, filed on Oct. 5, 2016.

(51) Int. Cl.
*G16H 50/20* (2018.01)
*G06N 7/00* (2006.01)
(Continued)

(52) U.S. Cl.
CPC ......... *G16H 50/20* (2018.01); *G06F 16/2471* (2019.01); *G06N 5/047* (2013.01); *G06N 7/005* (2013.01); *G06N 20/00* (2019.01)

(58) Field of Classification Search
None
See application file for complete search history.

(56) References Cited

U.S. PATENT DOCUMENTS

| 8,068,993 | B2 | 11/2011 | Karlov et al. | |
|---|---|---|---|---|
| 2009/0171871 | A1* | 7/2009 | Zhang | G06N 7/005 706/12 |

(Continued)

FOREIGN PATENT DOCUMENTS

| WO | WO2016094330 | 6/2016 |
|---|---|---|
| WO | WO2018090009 | 5/2018 |

(Continued)

OTHER PUBLICATIONS

Speiser et al., "Random Forest Classification of Etiologies for an Orphan Disease", Statistics in Medicine, 34, 887-899, doi: 10.1002/sim6351, Year: 2015.

(Continued)

*Primary Examiner* — Robert W Morgan
*Assistant Examiner* — Andrew E. Lee
(74) *Attorney, Agent, or Firm* — Heslin Rothenberg Farley & Mesiti P.C.; Kristian E. Ziegler, Esq.; Rachel L. Pearlman, Esq.

(57) ABSTRACT

A method, computer program product, and system identifying a probability of a medical condition in a patient. The method includes a processor obtaining data set(s) related to a patient population diagnosed with a medical condition and based on a frequency of features in the data set(s), identifying common features and weighting the common features based on frequency of occurrence in the data set(s) to generate mutual information. The processor generates pattern(s) including a portion of the common features to generate a machine learning algorithm(s). The processor compiles a training set of data to use to tune the machine learning algorithm(s). The processor dynamically adjusts common features in the pattern(s) such that the machine learning algorithm(s) can distinguish patient data indicating the medical condition from patient data not indicating the (Continued)

medical condition. The processor applies the machine learning algorithm(s) to data related to the undiagnosed patient, to determine the probability.

19 Claims, 10 Drawing Sheets

(51) Int. Cl.
    *G06N 5/04*     (2006.01)
    *G06N 20/00*     (2019.01)
    *G06F 16/2458*     (2019.01)

(56) References Cited

U.S. PATENT DOCUMENTS

| | | | |
|---|---|---|---|
| 2012/0271612 A1* | 10/2012 | Barsoum | G06F 19/00 703/11 |
| 2013/0071860 A1 | 3/2013 | Hale et al. | |
| 2013/0238533 A1* | 9/2013 | Virkar | G06N 20/10 706/12 |
| 2013/0262357 A1 | 10/2013 | Amarasingham et al. | |
| 2014/0095201 A1 | 4/2014 | Farooq et al. | |
| 2014/0222349 A1* | 8/2014 | Higgins | G16B 20/00 702/19 |
| 2014/0278448 A1 | 9/2014 | Sadeghi et al. | |
| 2014/0279746 A1* | 9/2014 | De Bruin | G16H 20/70 706/12 |
| 2014/0288440 A1* | 9/2014 | Asher | A61B 5/082 600/484 |
| 2015/0324527 A1* | 11/2015 | Siegel | G16B 50/00 705/3 |
| 2016/0063212 A1 | 3/2016 | Monier et al. | |
| 2017/0053665 A1* | 2/2017 | Quatieri, Jr. | G10L 25/66 |
| 2017/0124269 A1* | 5/2017 | McNair | G16H 10/60 |
| 2017/0198349 A1* | 7/2017 | Rice | G01N 33/6896 |
| 2017/0262604 A1 | 9/2017 | Francois | |
| 2017/0286622 A1* | 10/2017 | Cox | G06F 19/00 |
| 2017/0308981 A1 | 10/2017 | Razavian et al. | |
| 2019/0019581 A1* | 1/2019 | Vaughan | A61B 5/486 |
| 2019/0138693 A1 | 5/2019 | Mueller et al. | |
| 2019/0371463 A1* | 12/2019 | Asthana | G16H 50/70 |
| 2020/0151627 A1 | 5/2020 | Shukla et al. | |
| 2020/0294665 A1* | 9/2020 | Neumann | G16H 70/60 |

FOREIGN PATENT DOCUMENTS

| | | |
|---|---|---|
| WO | WO2020102220 | 5/2020 |
| WO | WO2020132468 | 6/2020 |

OTHER PUBLICATIONS

Huw Llewelyn, "Reasoning in Medicine and Science", Sep. 2015, https:/blog.oup.com/2013/09/medical-diagnosis-reasoning-probable-eliminationn/ (Acessed via Wayback machine).

Kvancz et al., "Predictive Analytics: A Case Study in Machine-Learning and Claims Databases", THe American Journal of Pharmacy Benefits, vol. 8, No. 6, Dec. 2016, 6 pages.

International Search Report and Written Opinion of International Application No. PCT/US2019/060962, dated Mar. 9, 2020, 9 pages.

International Search Report and Written Opinion for International Application No. PCT/US2019/067893, dated Mar. 15, 2020, 8 pages.

* cited by examiner

MACHINE-LEARNING BASED QUERY CONSTRUCTION AND PATTERN IDENTIFICATION FOR AMYOTROPHIC LATERAL SCLEROSIS

CROSS-REFERENCE TO RELATED APPLICATIONS

This application claims priority to U.S. Provisional Application No. 62/404,338 filed Oct. 5, 2016, entitled, "MACHINE-LEARNING BASED QUERY CONSTRUCTION AND PATTERN IDENTIFICATION" which is incorporated herein by reference in its entirety.

FIELD OF INVENTION

The invention relates to the creation and utilization of machine-based learning algorithms to establish and identify data patterns in the absence of established knowledge regarding these patterns.

BACKGROUND OF INVENTION

Health patterns indicative of certain health conditions are often difficult to identify. This is true for diseases and medical conditions that are readily known to the general population, as well as with diseases that are so rare that they affect only a small portion of the population.

Amyotrophic lateral sclerosis (ALS) is a clinical diagnosis of exclusion. The average delay in ALS diagnosis is one year after the appearance of the first symptom. This prolonged diagnostic time can be detrimental as it delays initiating approved treatments and the progression of the disease for an undiagnosed patient may preclude that patient, when finally diagnosed, from enrolling in a clinical trial. ALS is a progressive neurodegenerative disease that affects the motor neurons that connect the brain and spinal cord to muscles throughout the body. As motor neurons are lost, patients lose the ability to control voluntary muscle movement. Patients suffering from ALS often gradually experience difficulty walking, moving, speaking, swallowing, and breathing. Death often results from respiratory failure. There is currently no cure for ALS, and available treatments are only able to modestly slow its progression. ALS occurs in the US population at a rate ranging from 5 to 10 cases per 100,000.

A disease is defined as rare (orphan) if it affects fewer than 200,000 people in the US; there are about 7,000 types of such rare disorders. Most of these diseases are genetic, frequently misdiagnosed for years, and without FDA-approved drug treatment. Timely discovery of misdiagnosed and underdiagnosed patients is crucial for their survival and for the proper development and delivery of the right therapeutics (including niche drugs developed by pharmaceutical companies specifically for these rare conditions). The problem of finding potentially undiagnosed subjects for orphan diseases is that active surveillance for such conditions (canvassing a segment of population with questionnaires and/or tests) is expensive and impractical for rare (or even not so rare) diseases, and passive surveillance has to rely on existing medical records (produced by hospitals and insurance companies), which may be incomplete, unreliable, and not contain enough information relevant for the predictive diagnostics. Challenges in identifying these orphan diseases from population-related data exist based on both the limitations of present computing solutions to process the volume of data efficiently and the lack of knowledge regarding what parameters should be searched within this large volume.

The challenges related to establishing patterns that identify an event in a large volume of data and actually identifying that event in this large volume are not unique to disease or to orphan disease identification.

SUMMARY OF INVENTION

Shortcomings of the prior art are also overcome and additional advantages are provided through the provision of a method determining a probability of the presence of a given medical condition based on a data set related to a patient, the method includes: obtaining, by the one or more processors, one or more data sets related to a patient population diagnosed with an medical condition; based on a frequency of features in the one or more data sets, identifying, by the one or more processors, common features in the one or more data sets and weighting the common features based on frequency of occurrence in the one or more data sets, wherein the common features comprise mutual information; generating, by the one or more processors, one or more patterns comprising a portion of the common features; generating, by the one or more processors, one or more machine learning algorithms based on the one or more patterns, the one or more machine learning algorithms to identify presence or absence of the given medical condition in an undiagnosed patient based on absence or presence of features comprising the one or more patterns in data related to the undiagnosed patient; utilizing, by the one or more processors, statistical sampling to compile a training set of data, wherein the training set comprises data from the one or more data sets and at least one additional data set comprising data related to a population without the medical condition, and wherein utilizing the statistical sampling comprises formulating and obtaining queries based on the data set and processing and responding to the queries, the processing comprising, for each query: evaluating, by the one or more processors, the query to determine one of a high or a low level of anticipated complexity of a prospective response to the query; based on the query being evaluated at a low level of anticipated complexity, assigning, by the one or more processors, the query to a computing resource in the distributed computing environment, wherein the computing resource is configured to respond to low level complexity queries; and based on the query being evaluated at a high level of anticipated complexity, distributing, by the one or more processors, the query over a group of computing resources of the distributed computing environment to maximize efficiency, wherein the distributing comprises assigning each computing resource of the group of computing resources a portion of the query to execute in parallel with at least one other computing resource of the group of computing resources executing another portion of the query; tuning, by the one or more processors, the one or more machine learning algorithms by applying the training set of data to the one or more machine learning algorithms; dynamically adjusting, by the one or more processors, the common features comprising the one or more patterns to improve accuracy such that the one or more machine learning algorithms can distinguish patient data indicating the medical condition from patient data that does not indicate the medical condition; and determining, by the one or more processors, based on applying the one or more machine learning algorithms to data related to the undiagnosed patient, a probability, wherein the probability is a numerical value indicating a percentage of commonality between the data related to the undiagnosed patient and the one or more patterns.

Computer systems, computer program products, and methods relating to one or more aspects of the technique are also described and may be claimed herein. Further, services relating to one or more aspects of the technique are also described and may be claimed herein.

Additional features are realized through the techniques of the present invention. Other embodiments and aspects of the invention are described in detail herein and are considered a part of the claimed invention.

BRIEF DESCRIPTION OF DRAWINGS

One or more aspects of the present invention are particularly pointed out and distinctly claimed as examples in the claims at the conclusion of the specification. The foregoing and objects, features, and advantages of one or more aspects of the invention are apparent from the following detailed description taken in conjunction with the accompanying drawings.

DETAILED DESCRIPTION OF THE INVENTION

Figure 1:
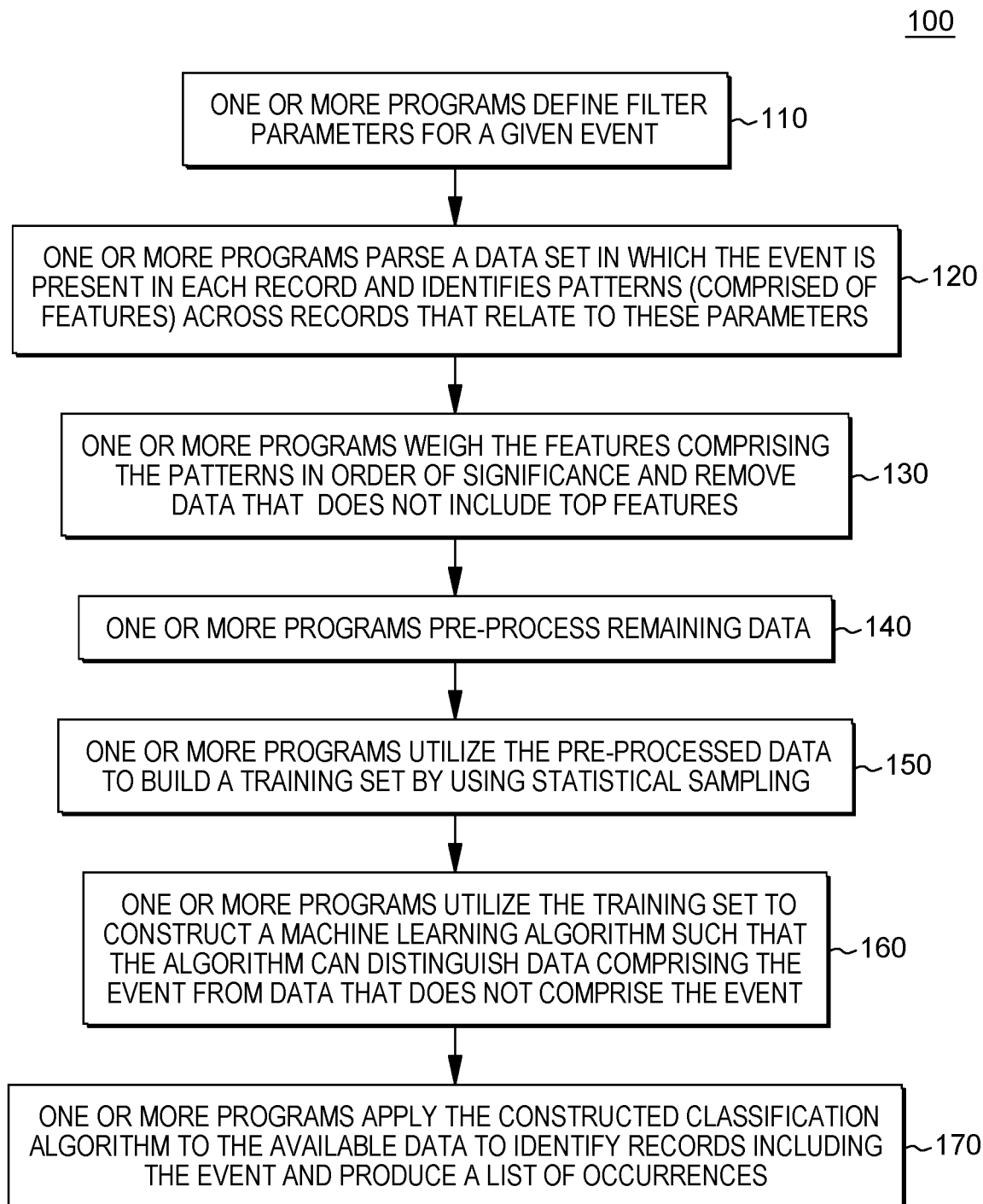
FIG. 1 depicts a workflow associated with aspects of embodiments of the present invention.

Aspects of the present invention and certain features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the invention in detail. It should be understood, however, that the detailed description and the specific examples, while indicating aspects of the invention, are given by way of illustration only, and not by way of limitation. Various substitutions, modifications, additions, and/or arrangements, within the spirit and/or scope of the underlying inventive concepts will be apparent to those skilled in the art from this disclosure. The terms software, program code, and one or more programs are used interchangeably throughout this application.

The term "diagnose" is utilized throughout the application in to suggest that a data model that is generated and method determining a probability of the presence of a given physical or medical condition, including but not limited to a disease or an orphan disease, based on a data set related to an individual, referred to herein as a patient. However, the so-called diagnosis provided by aspects of embodiments of the present invention is not analogous to a medical diagnosis, provided by a health professional, often based on the result of a medical text or procedure. Rather, a diagnosis herein is merely a recognition of a pattern, or a given portion of a pattern, where the pattern was generated from a self-learning model, in embodiments of the present invention.

Embodiments of the present invention combine data analytics and pattern prediction to enable program code executing on at least one processor to identify patterns within a data set in the absence of advance data defining the pattern. In an embodiment of the present invention, program code analyzes a data set to identify parameters comprising data points characteristic of a certain condition (e.g., a physical condition). The program code adapts a machine learning algorithm to utilize these parameters to identify data consistent with this condition and utilizing data sets of sizes which cannot be analyzed by a human or by a computing environment that does not adequately distribute processing tasks related to the analysis. The program code identifies these parameters in the absence of established data characterizing the condition. This approach can be utilized to determine recognition patterns to identify diseases (e.g., ALS), and/or orphan diseases in a data set that includes data related to individuals with this condition and subsequently, to identify these patterns in an unlimited data set where the prevalence of individuals with this condition is unknown. However, this approach is not merely limited to physical condition (e.g., disease) identification, but can be utilized in general to predict criteria identifying an event and apply these criteria across a data set that is not constrained by size or complexity. Throughout this specification, aspects of embodiments of the present invention are applied to the task of physical condition (e.g., disease) identification, including but not limited to ALS identification. However, this singular (non-limiting) application of aspects of embodiments of the present invention is offered to illustrate the functionality of the present invention, as understood by one of skill in the art.

Advantages provided by aspects of some embodiments of the present invention include: (1) the ability to identify features that differentiate ALS patients from the general population prior to diagnosis, (2) the ability to determine potential predictors of a future ALS diagnosis, (3) the ability to demonstrate the appearance of ALS symptoms earlier than currently understood by the medical community, and (4) the ability to provide the potential to accelerate ALS diagnosis.

Certain embodiments of the present invention represent improvements over known methods of data identification both in the application of identifying individuals with physical/medical conditions as well as in data management and data mining in general. For example, embodiments of the present invention enable the determination and identification of patterns based on an unlimited number of factors given the ability of the program code to mine large data stores. For example, when applied to creating a profile (e.g., a disease profile) and identifying individuals that fit this profile, relevant features that the program code builds into a pattern for later identification of individuals that fit this pattern are not solely based on diseases, but on drugs and procedures as well, which expands the information content that can be leveraged by the overall process. Embodiments of the present invention increase computational efficiency because, when building a profile to identify a given quality, the program code selects relevant features using not just prior knowledge and frequency count, but ultimate information theory mechanisms, including mutual information, and weight the variety of information utilized by, for example, truncating a the set of obtained features to establish a level of significance for each identified feature in the mutual information.

Mutual information is an example of a method that can be utilized to identify features in an embodiment of the present invention. Further embodiments of the present invention utilize varying techniques to select features, including but not limited to, diffusion mapping, principal component analysis, recursive feature elimination (a brute force approach to selecting features), and/or a Random Forest to select the features. Embodiments of the present invention that utilize mutual information, diffusion mapping, and a Random Forest may provide certain efficiency advantages.

Aspects of embodiments of the present invention represent improvements to existing computing technology and are inextricably tied to computing. Specifically, embodiments of the present invention represent improved methods of handling large volumes of data and for building logistical models from the data. For example, embodiments of the present invention reduce the observed data rate in the eventual results because the program code preprocesses the data utilized to build a pattern, rather than using a less efficient binary binning procedure.

Aspects of embodiments of the present invention are inextricably tied to computing at least because the electronic disease models generated by embodiments of the present invention cannot be generated outside of computing and do not exist outside of computing. Records initially utilized in embodiments of the present invention are electronic records in one or more data set, contained in one or more database, that are machine readable. The resultant models are also electronic and can only be applied to additional electronic data sets utilizing computing resources. Because of both the volume and the nature of data, an individual is not capable of accomplishing the specific aspects of embodiments of the present invention that result in a machine readable data model that can be applied by program code to additional data sets in order to identify records with a probability of an event or condition that the model was generated to predict the probable presence of. To be useful, program code in embodiments of the present invention both generates and updates models and provides results (identification of records that comport with the model), within a limited temporal period. For example, in a scenario where an individual visits a healthcare provider, the individual and the provider would benefit from acquiring information regarding whether the individual, as represented by an electronic medical record, has items in the record that match the data sought by one or more disease models. If this information cannot be provided within the visit, it is arguably not useful to the individual or the healthcare provider. Thus, in embodiments of the present invention, the program code analyzes an individual record and applies disease models in real-time, or close to real-time.

In certain embodiments of the present invention the program code predicts and detects patterns in data by utilizing Support Vector Machines (SVMs). In an aspect of an embodiment of the present invention, the program code trains a linear SVM classification algorithm for segregating database entries, for example, to separate entries representing individuals with a given condition from entries representing individuals that do not have the condition. In an embodiment of the present invention, the program code utilizes linear SVM, rather than, for example, logistic regression, Random Forest (RF) grouping algorithms, and/or other simple statistical approaches, to achieve a best available classification performance. Another advantage of certain embodiments of the present invention that utilize SVM is that the program code can apply the SVM score of the false positive data as a mechanism to sort out the most promising subjects. (Certain embodiments of the present invention do utilize RF grouping algorithms and logistic regression with SVM in order to achieve hyper-parameter optimization.)

Embodiments of the present invention provide advantages and improvements that are inextricably tied to computer technology also because embodiments of the present invention offer certain advantages that increase computational efficiency and efficacy. For example, as described in greater detail later on, embodiments of the present invention utilize distributed processing based on anticipated query results in order to decrease the timeline for key analytic deliverables. This distributed processing enables the program code to perform multiple analysis processes simultaneously. Portions of certain embodiments of the present invention can be migrated to a cloud architecture and made available to users as software as a service (SaaS) offerings. The unlimited computational capacity of resources in a cloud architecture are suited to support the program code's distribution of simultaneous queries and processes in order to meet the efficiency demands of the system in a data rich environment.

Embodiments of the present invention also provide advantages and improvements that are inextricably tied to computer technology because they utilize machine learning. One advantageous aspect of some embodiments of the present invention over existing approaches to event (e.g., condition) identification in data dense environments is that some other methods approach the problem of event identification and recognition as a statistical problem, instead of a machine learning one, which is an approach that limits the options in available tools. By utilizing machine learning, embodiments of the present invention can identify records that include an event where the information directly identifying the event is absent. For example, by using machine learning, program code can identify patients with a given disease in a data set of undiagnosed patients, i.e., where the data does not already indicate that the disease is present in the patient. In some cases, the program code can utilize machine learning to indicate that an individual is infected with a disease when the opposite is indicated in data related to that individual. Thus, the program code is not merely identifying and retrieving existing established data stored in one or more memory device. Rather, the program code establishes a pattern, continuously trains a machine learning algorithm to apply the pattern, and utilizes the algorithm to identify instances of an event not already explicitly indicated by the data utilizing this pattern.

Embodiments of the present invention provide advantages over known diagnostic systems when utilized to determine mutual information and apply this information to an analysis of a data set where the presence of the event related to the mutual information is unknown, at least because the process is devoid of selection bias. Returning to the orphan disease example, in embodiments of the present invention, there are no assumptions regarding an individual that are carried into the program code and the program code performs its analyses consistently. Selection bias is an issue when attempting to identify a medical condition as a medical professional may be prone to certain conclusions based on, for example, past experience. In the area of orphan disease identification, this bias is especially problematic because the rarity of an orphan disease means that a medical professional may come into contact with very few people, or even no people at all, with a given condition until a certain patient presents the condition.

As aforementioned, challenges in identifying conditions, including diseases, such as ALS, and orphan diseases, from population-related data exist based on both the limitations of present computing solutions to process the volume of data efficiently and the lack of knowledge regarding what parameters should be searched within this large volume. In the case of orphan diseases, the small number of confirmed cases renders pattern building and recognition challenging, and in the case of ALS, the fact that a medical diagnosis is the result of eliminating other possibilities renders the same data problems. Regarding the volume of data, embodiments of the present invention can process a large number of patients coded with a large number of universe codes. For example, an embodiment of the present invention can be utilized to process the patient histories of more than 180 million patients, whose records may include up to 10 years of recorded healthcare history. Given the distributed nature of the processing architecture, the number of patients that can be processed/scored is only limited by storage, as the efficiency of the process enables the processing of increasingly large volumes of data.

Workflows of certain embodiments of the present invention can include three stages: data integration, pattern extraction, and population separation. Data integration refers to aspects of embodiments of the present invention in which the program code derives discriminating features of a first data set, where an event is present. For example, if the event is a certain orphan disease, or ALS, the program code may analyze records of individuals medically diagnosed with the orphan disease or ALS and extract discriminating features that describe the treatment journey of these patients.

Pattern integration refers to aspects of embodiments of the present invention in which the program code develops a pattern for identifying records with a given event based on using the most distinctive features extracted during data integration. For example, if the aforementioned orphan disease is the example, the program code would develop patterns describing the most distinctive features the program code extracted from the patient records.

Population separation refers to aspects of embodiments of the present invention where the program code utilizes the pattern to identify the event in one or more data store. For example, returning to the orphan disease example, by analyzing data resources including records identifying large populations, the program code identifies within the resources which patient clusters match the treatment pathways exhibited by the known sufferers.

Referring specifically to ALS, in utilizing aspects of embodiments of the present invention to build a data model related to ALS and applying that dynamic model to identify individuals that fit the model within a given probability, embodiments of the present invention enable identification of early predictors of ALS by using big data analytics of a large claims database. FIG. 1 is a workflow 100 that illustrates aspects of embodiments of the present invention, including one or more programs that perform data integration (e.g., patient definition), pattern extraction (e.g., feature extraction), and generate population separation maps (e.g., prediction).

As will be illustrated and discussed herein, one or more programs, executed by at least one processing resource, mined data utilizing various aspects of embodiments of the present invention to identified features in the electronic medical data of ALS patients, specifically within the electronic claim histories of the patients, that differentiate these patients from the general population, even before initial ALS diagnosis by a medical professional. One or more programs in embodiments of the present invention determine that ALS patients may present with clinically relevant symptoms suggestive of connective tissue disorders, skin disorders, and nonspecific neurological complaints five (5) years before ALS is diagnosed. The one or more programs determine that medically significant predictors seen in patients who were eventually diagnosed with ALS included, include, but are not limited to, nervous system disorders, hereditary and degenerative nervous system conditions, connective tissue disease, skin disorders, lower respiratory disease, gastrointestinal disorders, neurologist visits, orthopedic surgeon visits, gastroenterologist visits, non-traumatic joint disorder, otolaryngologist visits, and/or the use of riluzole, a glutamate blocker, prior to diagnosis. In analyzing electronic data in a database comprising five (5) continuous years of medical records (histories), the one or more programs determined that the frequency of ALS patient features increase over time. In some embodiments of the present invention, one or more programs apply the model generated utilizing the electronic medical data, to conduct an analysis of combinatorial features that differentiate undiagnosed ALS patients from the general population, to further characterize early predictors of ALS, and to optimize the algorithm differentiating patients with ALS prior to diagnosis.

As will be described in more detail below, and as illustrated utilizing FIGS. 1-3, in embodiments of the present invention, one or more programs obtain (exclusively) machine-readable electronic medical records of individuals who were previously medically diagnosed with ALS. The one or more programs analyze (mine) the data utilizing both frequency ranking and by identifying mutual information. Thus, the program code in embodiments of the present invention employs an analysis that utilizes two data-ranking methods: a frequency method and a mutual information method. The program code utilizes the mutual information measure to quantify the statistical relevance of every feature in the electronic data set(s) of medical records to a future ALS diagnosis. The program code computes the relative frequency of pertinent events to rank the differentiating features based on the mutual information measure. Based on frequency ranking and mutual information, the one or more programs identify distinguishing features in categories that include diagnoses, procedures, drugs, providers, and locations. Based on identifying the distinguishing features, the one or more programs generate predictors (e.g., an adaptive data model), that the one or more programs can apply to data sets where it is unknown whether the individuals represented have ALS, and based on applying the model, the one or more programs can identify probabilities of ALS being present among the individuals represented.

Returning to FIG. 1, FIG. 1 is an example of a workflow 100 of an embodiment of the present invention which includes, as described above, data integration, pattern extraction, and population separation. FIG. 2 provides an overview 200 of portions of FIG. 1, as the aspects of data integration, pattern extraction, and population separation are also illustrated in FIG. 2.

Figure 2:
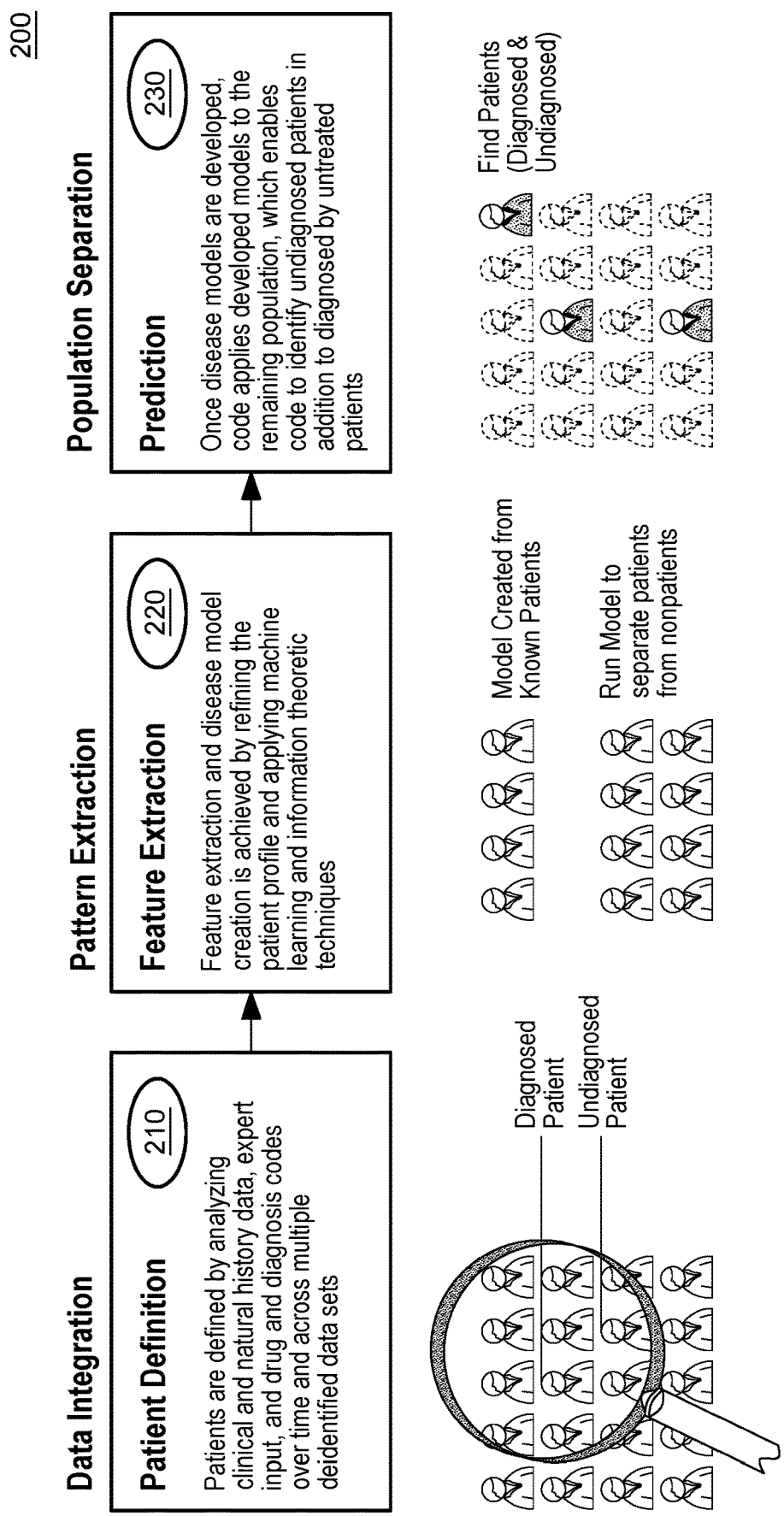
FIG. 2 depicts a workflow associated with aspects of embodiments of the present invention.

As seen in FIG. 2, data integration 210 includes patient definition, where one or more programs generating a patient definition by analyzing electronic records that include, but are not limited to, clinical and natural history data, expert input, and drug and diagnosis codes, over time, and across multiple de-identified data sets. The one or more programs in embodiments of the present invention perform pattern extraction 220, which the one or more programs extract features and create a disease (or event) model creation refining the patient profile and applying machine learning and information theoretic techniques. In population separation 230, the one or more programs make a prediction. Based on the one or more programs completing the development of disease models, the one or more programs applies the developed models to the remaining population, which enables the one or more programs to identify undiagnosed patients, in addition to diagnosed by untreated patients Returning to FIG. 1, in some embodiments of the present invention, the program code defines filter parameters for a given event (110). The filter parameters include data points where patterns could be relevant to the event. For example, if the event is the diagnosis of ALS, filter parameters may include one or more of disease/diagnostic codes for comorbid or symptomatic conditions (muscle weakness, dysphagia, other motor neuron diseases, multiple sclerosis, joint disorders, nervous system disorders, etc.), prescription drugs, inpatient and/or outpatient procedures to diagnose and/or treat symptoms of ALS (needle electromyography, physical therapy, magnetic resonance imaging, etc.), visits to specialists, etc. In an embodiment of the present invention, the disease/diagnostic codes may comprise diagnostic codes, such as International Statistical Classification of Diseases and Related Health Problems codes, referred to as ICD-9 codes and the newer ICD-10 codes.

Based on the filter parameters, the program code parses a data set in which the event is present in each record and identifies patterns (comprised of features) across records that relate to these parameters (120). Returning to ALS, the program code may identify mutual information of all categories of potentially relevant features such as, for example, for comorbid diagnoses, prescription drugs, provider visits, treatment locations, and/or medical procedures.

In an embodiment of the present invention, the data set analyzed by the program code comprises medical information (e.g., records) related to a population of individuals with a given disease. For example, the data set may include, coupled with the timing for each feature, diagnostic codes, $D_x(t)$, (e.g., ICD-9 codes, ICD-10 codes), procedures (e.g., Proc(t)), drug treatments, including prescriptions (e.g., Drug (t)), provider visits (Provider(t), and/or the location(s) of each individual represented in the data set (e.g., Location(t)). Locations may include, but are not limited to, locations of providers who interacted with a patient, a ZIP code related to a practice and/or a patient, a metropolitan area identifier, etc. The constant in the data set is that it is a known that each individual represented by the data has a specific medical condition, including a particular disease. The individual factors or features in the data set can also be referred to collectively as codes. One or more programs in an embodiment of a present invention may initially identify a population with ALSO by electronically isolating a group of records that include individuals definitively diagnosed with ALS, by utilizing ICD-9 code 335.20 (i.e., amyotrophic lateral sclerosis) and ICD-10 code G12.21 (i.e., amyotrophic lateral sclerosis) from all patients in the national dataset that includes the electronic medical records of over 170 million patients. In order to further isolate a data set for use in predictive feature analyses (e.g., population separation, FIG. 2, 230), the one or more programs filtered this initial data (110) by identifying, from these electronic records, records that represented individual across all the states in the United States with a minimum of one year of adjudicated claims history prior to the implementation of these ALS diagnosis code in the records. Codes for ALS may include connective tissue diseases, nervous system disorders, gastrointestinal disorders, joint disorders, multiple sclerosis, diagnostic nervous system procedures, physical therapy, magnetic resonance imaging, riluzole use, antibiotics, neurologist visits, etc.

Referring to FIG. 1 and the example of identifying a pattern ALS or for a given disease, including an orphan disease, in order to identify patterns (e.g., FIG. 1, 120), in an embodiment of the present invention, program code identifies a patient temporal signal, i.e., the codes and the combination of codes that separate individuals with a given condition, for example, from a general population. In an embodiment of the present invention, the program code utilizes feature selection techniques to identify the mutual information in the data set that can be utilized to characterize the given condition. The program code may utilize this mutual information as an inclusion/exclusion index. For example the codes selected through mutual information provide the inclusion criteria for patients to be selected by one or more programs and conversely, those patients who do not possess any of the codes within this set, are excluded by the one or more programs. The goal of feature selection is to define the smallest subset of features that collectively contain most of the mutually shared information and thus most clearly define the characteristics of a patient with a given disease. In building a dynamic electronic model for use in identifying individuals with ALS from electronic medical records, the one or more programs utilized a mutual information measure to quantify the statistical relevance of every feature in the electronic patient data set (e.g., records representing more than 170 million patients, of which diagnosis codes identified 13,882 ALS patients, each with records from 2010 through June 2016, with an average of 4.8 years of claims history per patient) to a future ALS diagnosis. Thus, the one or more programs determined the relative frequency of pertinent events to rank the differentiate features based on the mutual information measure.

In an embodiments of the present invention, the program code determined the distinguishing diagnoses by mutual information over five (5) years prior to an ALS diagnosis. From 48 to 60 months, the diagnoses, from most frequent to least frequent, were as follows determined by the program code to be as follows: other hereditary and degenerative nervous system conditions, other nervous system disorders, paralysis, medical examination/evaluation, multiple sclerosis (MS), other screening for suspected conditions (not mental disorders or infectious disease), other upper respiratory disease, other connective tissue disease, headache (including migraine), and spondylosis; intervertebral disc disorders; other back problems. From 36 to 48 months, the diagnoses, from most frequent to least frequent, were as follows determined by the program code to be as follows: other hereditary and degenerative nervous system conditions, other nervous system disorders, paralysis, spondylosis; intervertebral disc disorders; other back problems, other connective tissue disease, other screening for suspected conditions (not mental disorders or infectious disease), medical examination/evaluation, multiple sclerosis (MS), other non-traumatic joint disorders, and other upper respiratory disease. From 24 to 36 months, the diagnoses, from most frequent to least frequent, were as follows determined by the program code to be as follows: other nervous system disorders, other hereditary and degenerative nervous system conditions, other connective tissue disease, spondylosis; intervertebral disc disorders; other back problems, paralysis, multiple sclerosis (MS), other upper respiratory disease, malaise and fatigue, other gastrointestinal disorders, and other screening for suspected conditions (not mental disorders or infectious disease). For 18 to 24 months, the diagnoses, from most frequent to least frequent, were as follows determined by the program code to be as follows: other nervous system disorders, the diagnoses, from most frequent to least frequent, were as follows determined by the program code to be as follows: other hereditary and degenerative nervous system conditions, spondylosis; intervertebral disc disorders; other back problems, other connective tissue disease, paralysis, multiple sclerosis (MS), immunizations and screening for infectious disease, other gastrointestinal disorders, malaise and fatigue, and other non-traumatic joint disorders. For 12 to 18 months, the diagnoses, from most frequent to least frequent, were as follows determined by the program code to be as follows: other nervous system disorders, other hereditary and degenerative nervous system conditions, other connective tissue disease, spondylosis; intervertebral disc disorders; other back problems, paralysis, malaise and fatigue, other gastrointestinal disorders, multiple sclerosis (MS), other non-traumatic joint disorders, and rehabilitation care; fitting of prostheses; and adjustment of devices. For 9 to 12 months, the diagnoses, from most frequent to least frequent, were as follows determined by the program code to be as follows: other nervous system disorders, other hereditary and degenerative nervous system conditions, spondylosis; intervertebral disc disorders; other back problems, other connective tissue disease, paralysis, other gastrointestinal disorders, other non-traumatic joint disorders, malaise and fatigue, acquired foot deformities, and rehabilitation care; fitting of prostheses; and adjustment of devices. For 6 to 9 months, the diagnoses, from most frequent to least frequent, were as follows determined by the program code to be as follows: other nervous system disorders, spondylosis; intervertebral disc disorders; other back problems, other hereditary and degenerative nervous system conditions, other connective tissue disease, paralysis, malaise and fatigue, other gastrointestinal disorders, rehabilitation care; fitting of prostheses; and adjustment of devices, other non-traumatic joint disorders, and other lower respiratory disease. For 3 to 6 months, the diagnoses, from most frequent to least frequent, were as follows determined by the program code to be as follows: other nervous system disorders, spondylosis; intervertebral disc disorders; other back problems, other hereditary and degenerative nervous system conditions, other connective tissue disease, malaise and fatigue, other gastrointestinal disorders, paralysis, other upper respiratory disease, rehabilitation care; fitting of prostheses; and adjustment of devices, other non-traumatic joint disorders, and other lower respiratory disease. For 0 to 3 months, the diagnoses, from most frequent to least frequent, were as follows determined by the program code to be as follows: other nervous system disorders, other connective tissue disease, other hereditary and degenerative nervous system conditions, spondylosis; intervertebral disc disorders; other back problems, malaise and fatigue, other gastrointestinal disorders, paralysis, rehabilitation care; fitting of prostheses; and adjustment of devices, other upper respiratory disease, other lower respiratory disease.

By determining mutual information, the program code in embodiments of the present invention uncovers consistent data over voluminous records that would be impossible outside of the specialized processing, which is discussed herein. Based on identifying and ranking the mutual information above, the program code made certain discoveries regarding individuals with ALS that were not apparent before this analysis. The program code determined that connective tissue disease was significantly higher than the control population (ALS patients with the electronic data sets utilized) 5 years prior to ALS diagnosis. The code for muscle weakness was a significant driver of connective tissue disease diagnoses. Skin disorders were a prevalent code throughout the 5 years prior to diagnosis although they decreased in frequency as the patient neared ALS diagnosis. Other connective tissue disease, hereditary and degenerative nervous system conditions and other nervous system disorders were differentiating diagnoses throughout the 5 years leading up to ALS diagnosis. Connective tissue disease became a more prominent diagnosis as ALS diagnosis approached. Multiple sclerosis was one of the top differentiating diagnoses 5 years prior to ALS diagnosis, but diminished in prominence as ALS diagnosis approached. Malaise and fatigue and other gastrointestinal disorders appeared in the top ten differentiating diagnoses 36 months prior to ALS diagnosis, and increased in prominence as ALS diagnosis approached. Also, lower respiratory diseases did not appear in the top ten differentiating diagnoses until 9 months prior to ALS diagnosis.

Other commonalities determined in this ALS example by the program code include, but are not limited to: ALS patients are distributed throughout the US, with higher concentrations in the Northeast, Florida, and Great Lakes, compared to the general population, ALS patients are skewed to older age and male gender, the patient geographic distribution is in line with the US population, 26.7% of patients had claims data for riluzole, 56% of the patients with ALS were covered by commercial insurance plans, 34% by Medicare, and 10% by Medicaid.

As discussed above, the program code applies frequency ranking and mutual information procedures in embodiments of the present invention to identify the distinguishing features that include diagnoses, procedures, drugs, providers, and locations, which the program code later uses to determine predictors of the condition. Thus, with ALS, the program code, in determining the distinguishing features utilizing these techniques also determined: visits to the neurologist become much more common as patients near ALS diagnosis; visits to the gastroenterologist become less frequent relative to other providers in the 2 years prior to ALS diagnosis; visits to orthopedists had little change over time, while visits to otolaryngologists increased slightly; initially, visits to both orthopedic surgery and gastroenterology are common, but gastroenterology visits declined as patients neared diagnosis; and visits to the otolaryngologist increased as patients neared ALS diagnosis. Also, the program code determined that ALS patients more frequently saw orthopedists than neurologists between 18 and 60 months prior to diagnosis.

The program code may also take into account feature continuity when determining predictors. In the ALS example, the program code, in its analysis to identify distinguishing features, determined that ALS patient features increased over time in the 5-year cohort, other nervous system disorders and other connective tissue disease increased disproportionately as patients approached diagnosis, and that unspecified disease of spinal cord and primary lateral sclerosis changed relatively little over time.

Using the described analytic methods, the program code identified features in ALS patients' claims histories that differentiate them from the general population before initial ALS diagnosis. The program code determined that medically significant predictors seen in patients who were eventually diagnosed with ALS included, but were not limited to, nervous system disorders, hereditary and degenerative nervous system conditions, connective tissue disease, skin disorders, lower respiratory disease, gastrointestinal disorders, neurologist visits, orthopedic surgeon visits, gastroenterologist visits, non-traumatic joint disorder, otolaryngologist visits, and the use of riluzole prior to diagnosis. As is discussed herein, upon identifying the differentiated features, the program code analyzes combinatorial features that differentiate undiagnosed ALS patients from the general population to further characterize early predictors of ALS, and optimize the algorithm differentiating patients with ALS prior to diagnosis.

Returning to the analysis to generate the predictive model, in embodiments of the present invention, as discussed above, for each category represented in the data set, the program code analyzes items in those categories over time and notes the absence or presence of each item that appears in the data set for each category. Returning to the disease example, in an embodiment of the present invention, the program code separately analyses codes in each of the following categories: $D_x(t)$, Proc(t), Drug(t), Provider(t), Location(t)). The one or more programs considered features including diagnosis codes, procedure codes, medications, standard provider types, and standard care facility types. Specific items in these categories for ALS may include, but not be limited to, connective tissue diseases, nervous system disorders, gastrointestinal disorders, joint disorders, and multiple sclerosis ($D_x(t)$), diagnostic nervous system procedures, physical therapy, and magnetic resonance imaging (Proc(t)), riluzole and antibiotics (Drug(t)), neurologist, gastroenterologist, and orthopedist visits (Provider(t)), and office, outpatient facility, and patient home (Location(t)).

Table 1 below illustrates an analysis of the program code of the presence and absence of certain items in a given category utilizing the orphan disease identification example. In Table 1, the variables 1 and 0 serve as categorical variables and represent whether the given item is absent or present at a given time. In the example of Table 1, the diagnosis codes assigned to individuals by medical professionals, in the data set, over time, are analyzed by the program code. In an embodiment of the present invention, the program code repeats this analysis for procedures, drugs, and the locations of the individuals represented in the records in the data set. As is understood by one of skill in the art, program code performing the analysis can identify nuances in the vast data set within a workable timeframe (e.g., during the visit of an individual to a health care provider) based on the utilization of the processing power of the computer system upon which aspects of the present invention are implemented. FIGS. 4-7, which will be discussed herein, include computing configurations that are customized to handle the processing demands that the analysis performed by the program code utilizes

TABLE 1

| Pat(N) | $t_1$ | $t_2$ | $t_3$ | ... | $t_n$ |
|---|---|---|---|---|---|
| $D_x1$ | 1 | 0 | 1 | | 1 |
| $D_x2$ | 0 | 1 | 0 | | 0 |
| ... | | | | | |
| $D_xn$ | 1 | 1 | 1 | | 1 |

Referring back to FIG. 1, once the program code has identified patterns, in an embodiment of the present invention, the program code may weigh the features comprising the patterns in order of significance and remove data that do not include top features (130). Embodiments of the present invention employ more than one method of weighing and selecting significant features. As discussed in relation to the ALS example above, the program code may ranking the features based on the raw mutual information values. However, in some embodiments of the present invention, the program code may view the output of a classifier, e.g., SVM or random forest that will provide a numerical measure of the feature importance that can then be ranked. In an embodiment of the present invention, the program code may weigh a feature with more mutual information across records as more significant. Thus, the program code selects top features (i.e., features with largest values of mutual information, down to the level of significance) from each of the categories and orders them in descending order (according to the values of mutual information). By removing data that does not include top features, the program code focuses the analysis and increases the efficiency in later identifications. The universe of data related to, for example, individuals suffering from an orphan disease, may be extremely vast, and by weighing features of the data, the program code is able to consolidate the data set into a more manageable amount for processing. In an embodiment of the present invention, the program code determines the frequency of a code and represents this frequency with a number between 0 and 1. The program code utilizes these frequency codes to perform binning based on how often each item occurs within the data set.

For ease of understanding, Table 1 displays binary values (1 and 0), however, a data set that is analyzed may include more than one event in a specific time slot, thus, a binary representation, such as Table 1 is not fully representative of this aspect of an embodiment of the present invention and is offered merely for ease of understanding. In fact, for a specific condition or disease, the table would not be binary, but would contain numerical values as the numerical values would represent frequency of a code appearing in a patients' health journey. In an embodiment of the present invention, the values in a matrix can represent the presence or absence of a code in a patient's history (as seen in Table 1), but can also represent the frequency with which the code occurs in that time slot. For example, if each column represents a month, then the numerical value can represent (1) the absence or presence of a code, (2) the number of times that code appears in that time slot, (3) the average frequency with which that code appears in that time slot, and (4) any function that can be applied to the value to represent events in that time slot.

Aspects of embodiments of the present invention utilized to generate mutual information are the same regardless of the condition for which the program code is constructing this information. Thus, embodiments of the present invention are portable over an unlimited number of data sets and can be utilized to identify an unlimited number of events or conditions. As described above, the program code indexes tables in order to derive tables for use in the analysis and, as explained in FIGS. 4-7, the computing is distributed based on the processing demands of the processes performed by the program code to generate the mutual information. In embodiments of the present invention, the program code computes mutual information for each feature as an independent process. The program code computes mutual information a specific feature and an output class variable. Computing the mutual information of two features in separate processes will not affect the result of either computed mutual information result.

Returning to FIG. 1, in an embodiment of the present invention, the program code may pre-process remaining data (140). For example, in an embodiment of the present invention, the program code may use a binning procedure using the average value of the corresponding feature as threshold, for example, values above the threshold are coded as 1, and values below it as 0.

In an embodiment of the present invention, after pre-processing the remaining data, in embodiments where this part of the process is included, the program code utilizes the pre-processed data or access available data sets to build a training set by using statistical sampling (150). The training set includes data representing the event and data that represent an absence of the event. In some embodiments of the present invention, the training set comprises electronic records that are only readable by a computing resource.

The program code formulates the training set by proportionally selecting representative electronic records from the target and control populations: the target population is the population with the condition (e.g., event, disease) and the control population is the population is the negative case (to distinguish from the target). Thus, in the example where an event is a disease, the training set includes disease entries and healthy entries. Departing from the specific disease example, in an embodiment of the present invention, the program code utilizes a test set of training data to train the machine learning algorithm. The training set is selected to include both records with the occurrence or condition the algorithm was generated to identify, and records absent this occurrence or condition. The program code tests/trains the individual features that comprise the mutual information (and/or other technologies discussed herein) selected to identify a given condition, and utilizing voting and ensemble learning, trains the algorithm.

In an embodiment of the present invention, the program code may utilize the training set with the significant patterns identified in the analysis to construct and tune a machine learning algorithm, such that the algorithm can distinguish data comprising the event from data that does not comprise the event (160). The machine learning algorithm may be a linear SVM classification algorithm, which can be utilized with one or more of an RF grouping algorithm and/or a log regression. If the event is a disease, including an orphan disease, the program code may train the machine learning algorithm to separate database entries representing individuals with a disease from entries representing healthy individuals and/or individuals without this particular disease. The program code may utilize the machine learning algorithm, may assign probabilities to various records in the data set during training runs and the program code, may continue training the algorithm until the probabilities accurately reflect the presence and/or absence of a condition in the records within a pre-defined accuracy threshold. With certain diseases, the program code utilizes a support vector machine (SVM) classifier. The program code made a selection based on a comparative assessment of various classifiers. When building a model for ALS, in some embodiments of the present invention, the program code utilized random forest to generate predictors.

In some embodiments of the present invention, using the disease example, the training set represents a patient population that had the disease. This defined patient population may consist of a constellation of codes, (diagnosis, procedures, drugs, etc.). The machine learning algorithm, which is discussed herein, learns from this defined patient population. In essence, the machine learning algorithm uses a surrogate patient population to find the undiagnosed patients. Stated in another way, the surrogate patient population consists of the patients known to have the disease, and the machine learning algorithms encode their pre-diagnosis characteristics to find similar patients and process the retrospective patient journey to predict the prospective patient journey. In the patient definition process (see, e.g., FIG. 2, 220) the program code identifies cohort of patients that the machine learning algorithm will learn from; this patient cohort will serve as the training set. In embodiments of the present invention, the internal algorithms applied by the program code include, but are not limited to: 1) mutual information to inform or refine the patient definition; and/or 2) various datamining techniques, including but not limited to, histograms to capture procedures, drugs, diagnosis codes, specialty types, geographic location, patient demographics (age, gender), and co-morbidities.

As aforementioned, in an embodiment of the present invention, the program code constructs the machine learning algorithm, which can be understood as a classifier, as it classifies records (which may represent individuals) into a group with a given condition and a group without the given condition. In an embodiment of the present invention, the program code utilizes the frequency of occurrences of features in the mutual information to identify and filter out false positives. The program code utilizes the classifier to create a boundary between individuals with a condition and the general population to lower multi-dimensional planes, given multiple dimensions, including, for example, fifty (50) to one hundred (100) dimensions. When embodiments of the present invention are employed to build a model to predict ALS, the one or more program employ an ensemble of classifiers developed employing machine learning techniques to optimize the selection and ranking of ALS diagnosis predictors (see, e.g., FIG. 2, 230).

As part of constructing a classifier (machine learning algorithm), the program code may test the classifier to tune its accuracy. In an embodiment of the present invention, the program code feeds the previously identified feature set into a classifier and utilizes the classifier to classify records of individuals based on the presence or absence of a given condition, which is known before the tuning. As aforementioned, the presence or absence of the condition is not noted explicitly in the records of the data set. When classifying an individual with a given condition utilizing the classifier, the program code may indicate a probability of a given condition with a rating on a scale, for example, between 0 and 1, where 1 would indicate a definitive presence. The classifier may also exclude certain individuals, based on the medical data of the individual, from the condition.

In an embodiment of the present invention, the program code constructs more than one machine learning algorithm, each with different parameters for classification, based on different analysis of the mutual information, and generates an ultimate machine learning algorithm based on a sum of these classifiers.

In an embodiment of the present invention, to decrease the instances of false positive results, in an embodiment of the present invention, when the algorithm is an SVM algorithm, the program code collects false positive results and sorts them according to their SVM score in order to identify false positives. In an embodiment of the present invention, to increase the comprehensibility and usability of the result, the program code post-processes records identified as including the event according to pre-defined logical filters. These pre-defined filters may be clinically derived (e.g., only males have this disease). In the disease example, the result of applying the classification algorithm is a sorted list of individuals suspected of having the disease.

Departing from the specific disease example and returning to FIG. 1, based on training the machine learning algorithm, the program code applies the constructed classification algorithm to the available data to identify records, including the event, and produces a list of occurrences (170). In some embodiments of the present invention, the constructed classification algorithm is a database object that is stored in a memory resource that is communicatively coupled to the processing resource executing the program code. In some embodiments of the present invention, the list produced is a machine-readable data set that is saved by the program code in stored in a memory resource that is communicatively coupled to the processing resource, including but not limited to, a relational database. As discussed earlier, this process is illustrated in FIG. 2.

Figure 3:
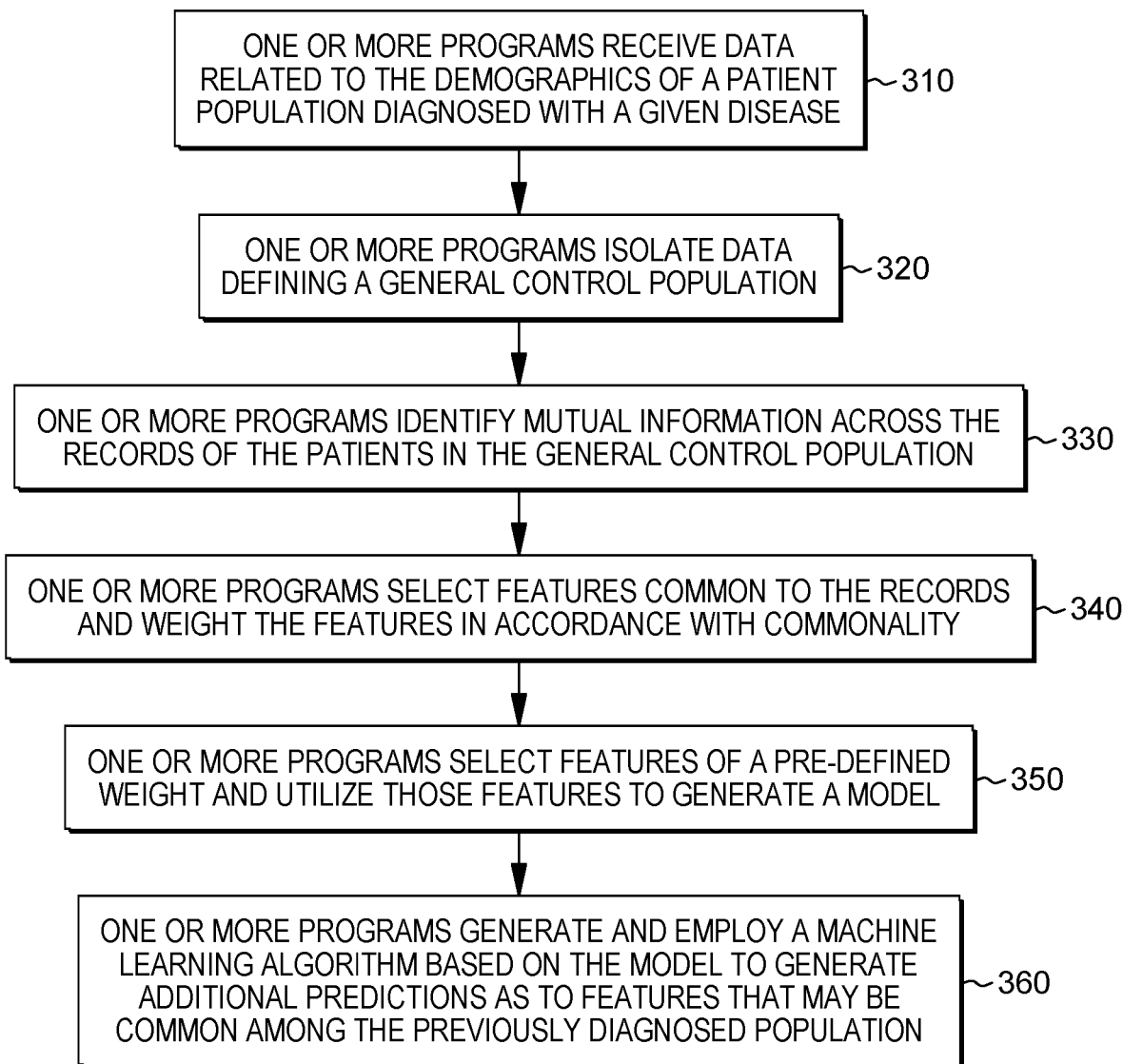
FIG. 3 depicts a workflow associated with aspects of embodiments of the present invention.

FIG. 3 is a workflow 300 of certain aspects of an embodiment of the present invention. In order to offer a comprehensive example of the operation of an embodiment of the present invention, FIG. 3 uses disease identification in population data as an example of the invention's capability in identifying events across one or more data set. Aspects of this workflow 300 are relevant to the specific ALS model disclosed herein. FIG. 3 also demonstrates how the machine learning utilized in the present invention is a continuous process and an evolving process. The training of an algorithm, including but not limited to, an SVM algorithm and/or a random forest algorithm, can be an ongoing and iterative process. For example, the algorithm may include a machine learning algorithm that is continuously trained by the program code as validated samples and their extracted patterns are applied to the training algorithms.

Referring to FIG. 3, the program code receives data related to a patient population diagnosed with a given disease (310). This data is provided in the form of machine-readable electronic medical records. Thus, the program code obtains the data. From the data, the program code isolates data defining a general control population (320). In an embodiment of the present invention, the control population serves as a negative example to the learning algorithm. In addition, the control population can incorporate clinically derived comorbidities to distinguish further the population with the disease from the population without the disease. The program code identifies mutual information across the records of the patients in the general control population (330). The program code selects features common to the records and weighs the features in accordance with commonality (340). The program code selects features of a pre-defined weight and utilizes those features to generate a machine learning algorithm (350). In an embodiment of the present invention, the program code selects features that meet a certain pre-defined threshold based upon the prevalence of the feature in the initial data set. In an embodiment of the present invention, the model defines a group of features for an individual with the disease.

The program code employs the machine learning algorithm to generate additional predictions as to features that may be common among the previously diagnosed population (360). Returning to the ALS example. The one or more programs in an embodiments of the present invention derived predictors (e.g., diagnosis predictors, see FIG. 2, 230) by differentiating features selected by mutual information and ranking/weighing the features utilizing relative frequency. In some embodiments of the present invention, the one or more programs may generate additional predictions by utilizing data in particular time periods. In building predictors for ALS, the one or more programs in an embodiment of the present invention generated predictors utilizing data within the following time brackets: 3, 6, 9, 12, 18, 24, 36, 48, and 60 months before the initial ALS diagnosis.

As will be understood by one of skill in the art, patterns or commonalities in the data among various individuals with a given condition may not be readily apparent when the program code scans the data. For this reason, the machine learning algorithm assists the program code in predicting what some commonalities may be, based on already-identified commonalities. The program code can then test whether these predictions represent actual patterns. When a prediction is sufficiently prevalent, the program code updates the pattern and therefore, the machine learning algorithm, to include this quality.

The identification of features, generation of a model, and generation of prediction for additional features, is an iterative process that tunes the machine learning algorithm that the program code ultimately utilizes to identify undiagnosed patients in an expanded data set. Additionally, the program code can utilize features derived from one data set in an analysis of another data set. Thus, based on the predictions, the program code selects features common to the records and weighs the features in accordance with commonality (340). The program code selects features of a pre-defined weight and utilizes those features to update the model (350). Thus, the machine learning aspect of an embodiment of the present invention is iterative.

As demonstrated in FIG. 3, not only does the program code train a machine learning algorithm based on weighted mutual information initially identified by the program code upon obtaining and/or receiving the data, the algorithm also generates predictions for data that may exist in the data set that was not initially identified, enabling the program code to further analyze the data based in these predictions, validate or invalidate the predictions, and based on this result, further train the algorithm to improve its ability to identify, for example, undiagnosed patients with a given disease.

Returning to FIG. 3, the program code applies the machine learning algorithm to identify undiagnosed individuals with a disease in a larger population (360).

In an embodiment of the present invention, the program code can align the determination of a diagnosis for a given individual with the timing of the diagnosis as related to items in the mutual information that match up with the data related to the individual.

An important challenge of identifying an isolated event in a data set utilizing a machine learning algorithm that can utilize unlimited parameters of varying complexity is that the computation can be extremely inefficient, as the algorithms scale non-linearly. Thus, when the program code trains and applies the machine learning algorithm to identify undiagnosed individuals with a disease in a larger population (360), in embodiments of the present invention, the queries utilized in the training and application of the algorithm are distributed to increase the efficiency of the process. Specifically, in an aspect of certain embodiments of the present invention, the program code receives queries throughout the process of identifying the events in the data set and evaluates the complexity of the queries before assigning a computer resource to answer the query. For example, in an embodiment of the present invention, the program code decides where to route a query based on the complexity of the anticipated answer to the query. In this manner, the program code sends a straightforward database query that can be answered with a single value pulled from a data set in response to a resource configured to respond efficiently to this type of query. Meanwhile, queries that require more complex responses, such as queries included in the execution of the machine learning algorithm, may be distributed over a group of resources to maximize efficiency, without compromising functionality.

In an embodiment of the present invention, the program code builds and improves the model through machine learning at a granular level. The model building code architecture is integrated in the sense that the only input needed is a list of patient IDs (de-identified patient ID numbers), and a list of features to include in the model. The model builder sets up the testing and training sets, extracts the appropriate retrospective patient histories from the database and builds a suite of models, optimizes them, ensembles them and then generates a report on their performance.

In an embodiment of the present invention, a database comprises a set of tables that are derived from the raw data obtained from the claims data vendor. This new data architecture combines the relevant data elements from all the "raw" tables and produces tables that contain only the pertinent information used for the machine learning models. The tables are indexed (internal database optimization) so that queries execute faster. In embodiments of the present invention, the program code derives a set of population tables from the raw tables, extracting data elements pertinent and representative of each patient's health journey. The extracted data includes, for each record, the diagnosis code, the date, the patient id number, the drug code, the procedure code, and all matched to the date on the claim. In embodiments of the present invention, separate tables exist for the diagnosis code, drugs code, procedure code, and the specialty type.

Figure 4:
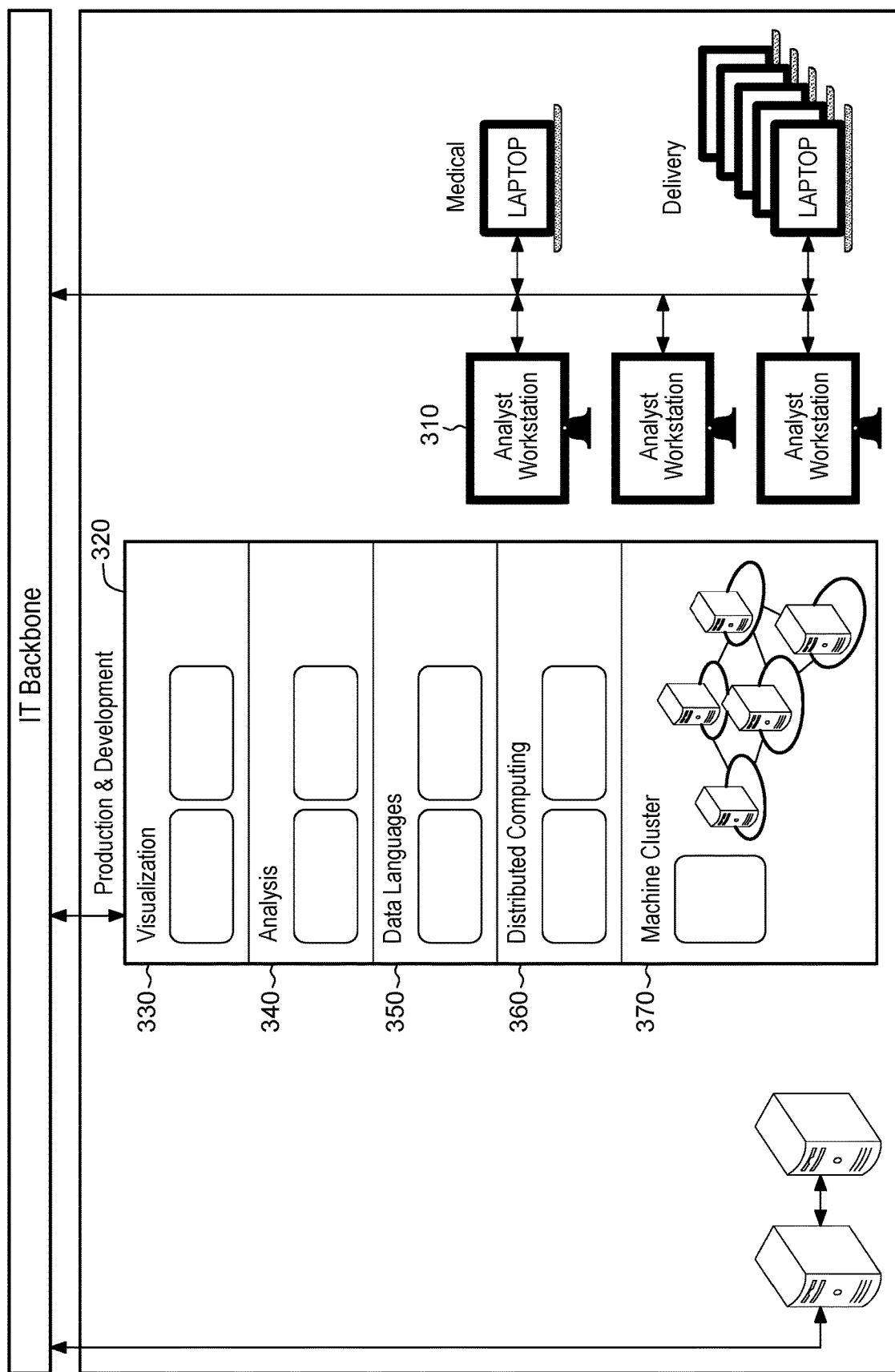
FIG. 4 depicts one example of aspects of a computing environment used to execute one or more aspects of an embodiment of the present invention.

FIG. 4 depicts a technical architecture that may be utilized by an embodiment of the present invention. In an embodiment of the present invention, a user utilizes a workstation 310 to connect to a distributed computing environment 320 over a network connection. The network utilized can be wired, wireless or hybrid and may be public or private, depending upon the data security employed in the delivery of the data. The network may include the Internet. The distributed computing environment is layered in order to service efficiently the queries and machine learning of the method. Layers includes a visualization layer 330 responsible for delivery of comprehensive results, an analysis layer 340 responsible for processing and responding to queries that require straightforward data access answers, a data language layer 350 to extract, transform, load, generate derived tables to increase efficiency, extract and prepare data for machine learning algorithms, and/or apply information theoretic techniques to extract all features, and a distributed computing layer 360 responsible for allocating resources for processing various threads utilized in embodiments of the present invention. The program code in the distributed computing layer 360 manages at least one server 370 (the cluster of five servers in FIG. 4 is merely one example used to illustrate and is not limiting). The distributed computing layer 360 receives each query and/or instruction and the program code in the distributed computing layer decides, based on the type of response the query requests or the complexity of the instruction, whether to distribute the query or instruction to a resource in of the managed resources 370 and to which resource the query/instruction should be distributed.

Figure 5:
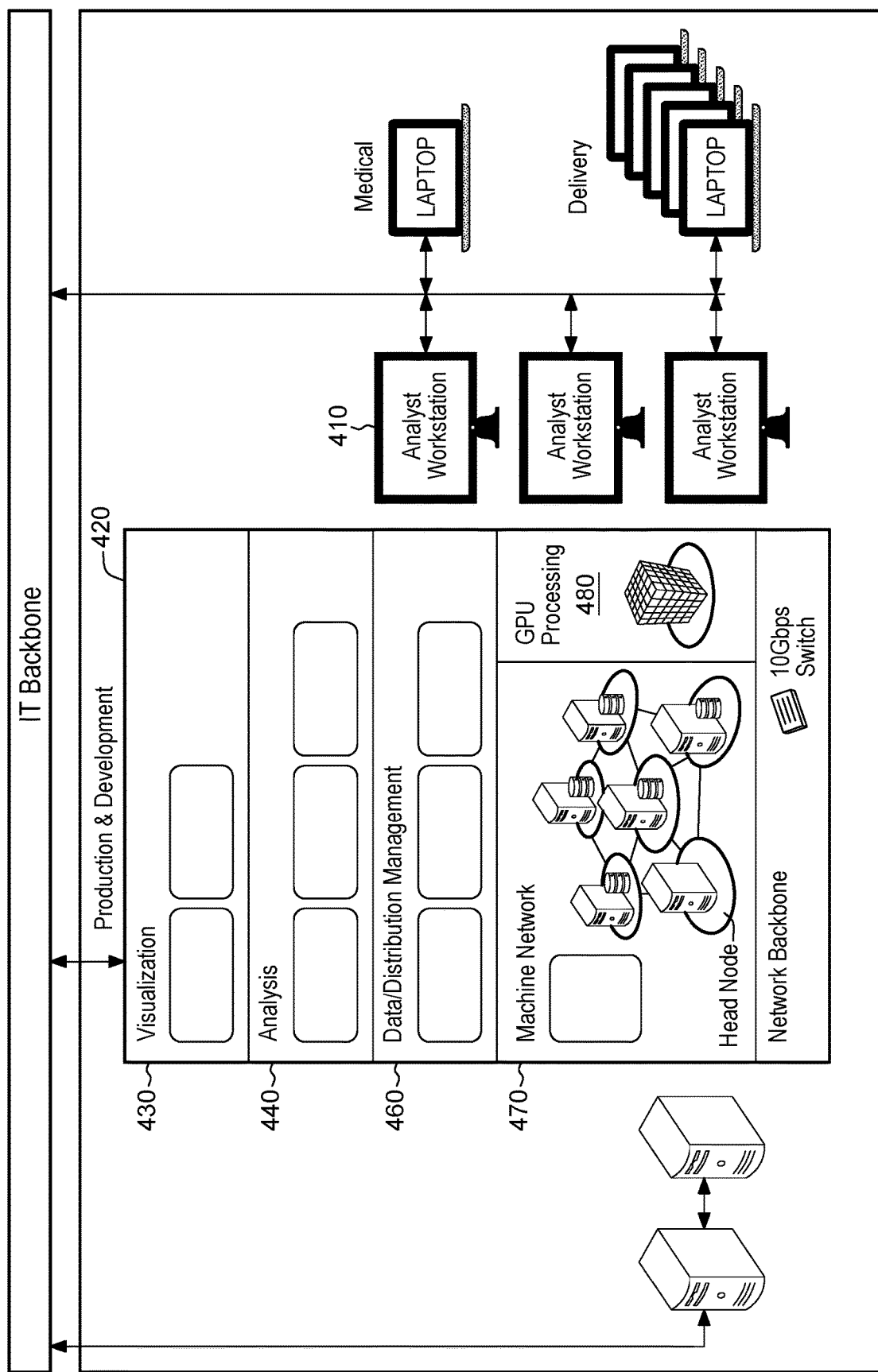
FIG. 5 depicts one example of aspects of a computing environment used to execute one or more aspects of an embodiment of the present invention.

FIG. 5 depicts another architecture that can be utilized by embodiments of the present invention. In this technical environment, rather than a data languages layer, a combined data/distribution management layer 460 layer manages distribution to the managed resources 470, as well as to at least one dedicated processing resource 480, which handles the machine learning. This dedicated processing resource 480 can handle multiple threads simultaneously. At the data/distribution management layer, the program code receives a query and based on the type of response the query is requesting, the program code decides whether to distribute the query to the managed resources 470 or to answer the query with the resource in the data/distribution management layer 460. In embodiments of the present invention, general database queries are handled by resources at the data/distribution management layer 460 without further distribution. In addition, the distributing functionality, program code executing on resources in the data/distribution management layer 460 also interact with the dedicated processing resource to select the parameters utilized in the machine learning.

Figure 6:
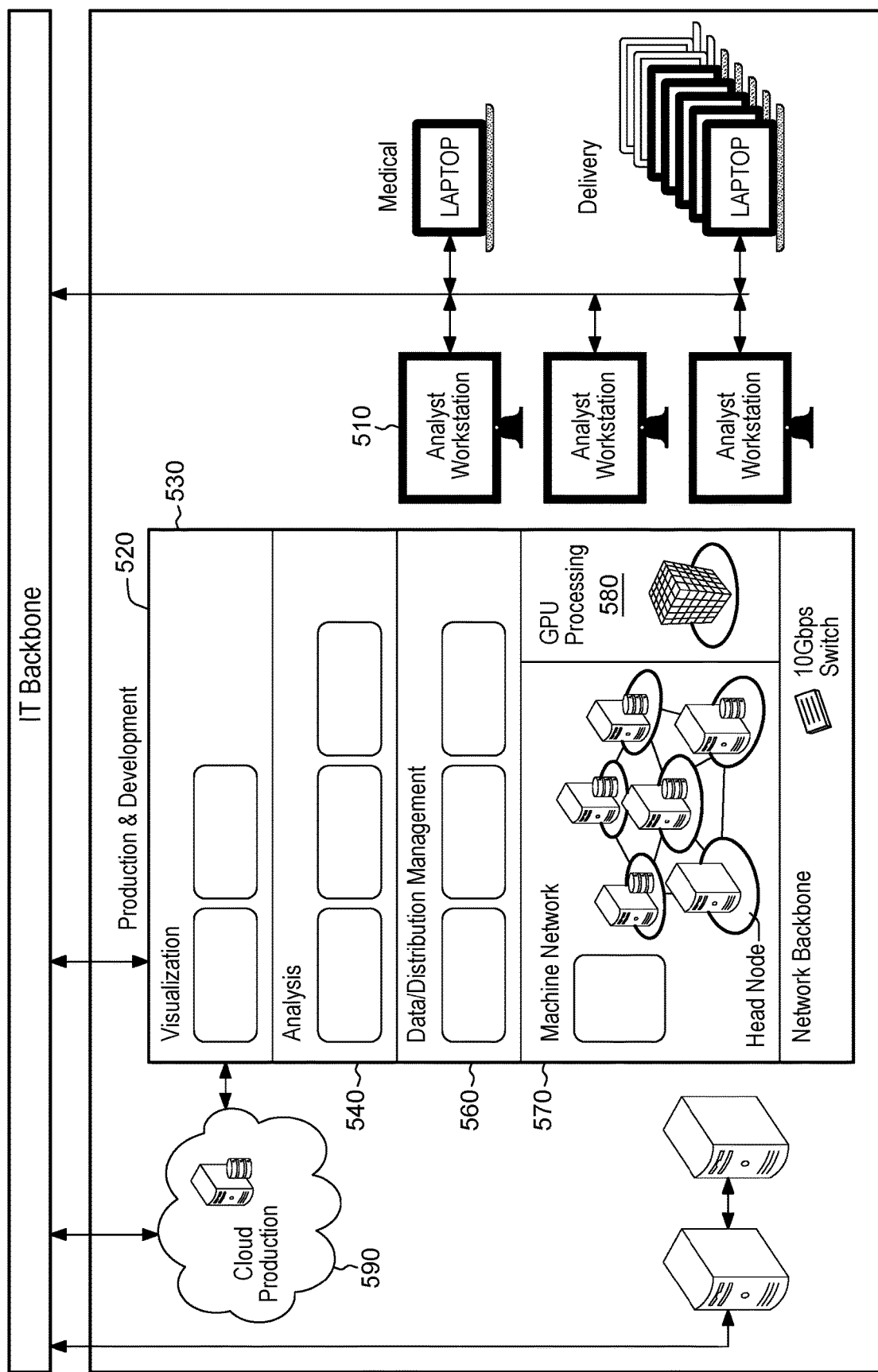
FIG. 6 depicts one example of aspects of a computing environment used to execute one or more aspects of an embodiment of the present invention.

FIG. 6 is one example of a computing environment utilized by some embodiments of the present invention that includes elements of a cloud 590. In this example, the program code utilizes the resource of the cloud 590 to pre-populate data at rest so that the data utilized by the program code in the present invention both to train the machine learning algorithm and ultimately to identify records with a given event (e.g., disease) is unlimited. Aspects of certain embodiments of the present invention can be deployed as SaaS utilizing this cloud 590 environment.

Figure 7:
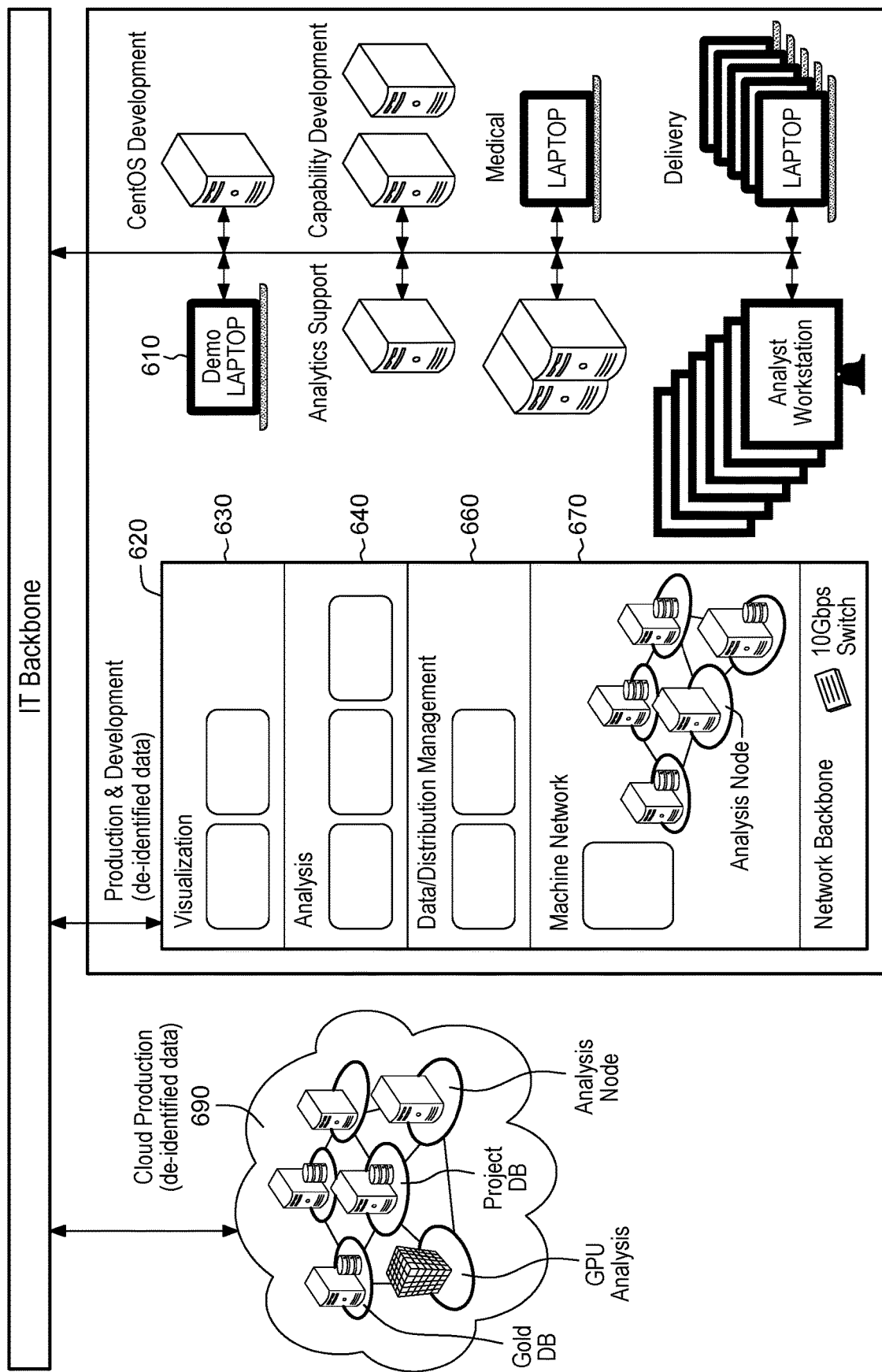
FIG. 7 depicts a workflow associated with aspects of embodiments of the present invention.

FIG. 7 is another examples of a technical environment that can be a portion of an embodiment of the present invention. In this example, as with FIG. 6, the present invention that includes elements of a cloud 590. In this example, as with FIG. 6, the program code utilizes the resource of the cloud 590 to pre-populate data at rest so that the data utilized by the program code in the present invention both to train the machine learning algorithm and ultimately to identify records with a given event (e.g., disease) is unlimited. Aspects of certain embodiments of the present invention can be deployed as SaaS utilizing this cloud 590 environment. Utilizing the technical architecture of this figure, program code will execute: (1) on the 5 machine network, and/or (2) on AWS cloud computing infrastructure.

Figure 8:
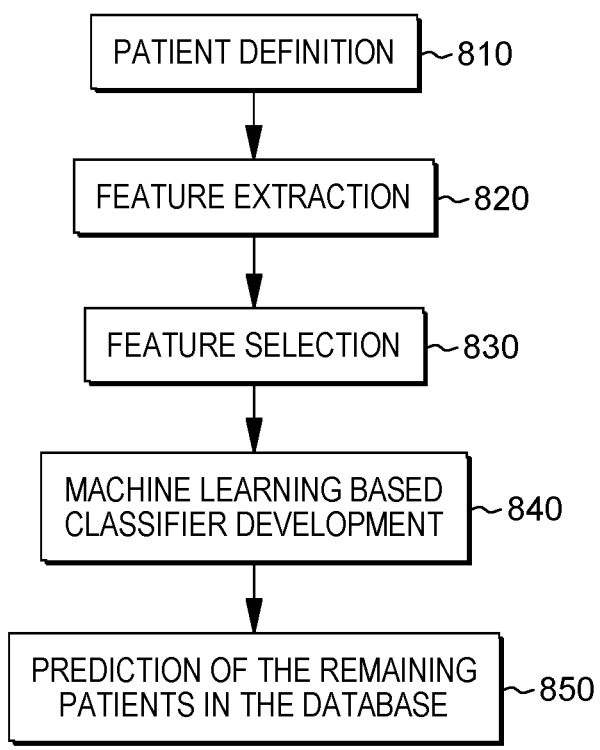
FIG. 8 depicts one example of aspects of a computing environment used to execute one or more aspects of an embodiment of the present invention.

FIG. 8 is a general workflow 800 that illustrates aspects of various aspects of some embodiments of the present invention. This workflow 800 provides a general guide to certain features of embodiments of the present invention. Each aspect of this workflow 800 is performed by program code executed by at least one processing circuit. As illustrated in FIG. 8, the program code performs patient definition 810, feature extraction 820, feature selection 830, machine learning based classifier development 840, and prediction of the remaining patients in the database 850.

The application of certain aspects of embodiments of the present invention to the identification of diseases can be understood in the context of the example that follows. Below, for ALS, data related to the demographics of a patient population diagnosed with ALS was obtained by one or more programs from a database of de-identified patient claims data acquired from an insurance claims database. For example, a database utilized in an embodiment of the present invention may comprise data covering eight years. An embodiment of the present invention was utilized to discover patients within this database who had not yet been diagnosed with ALS. Although ALS is used specifically in this example, the process is also relevant to a generic Disease 1. The description is therefore genericized in order to illustrate the functionality.

Stage 1: Patient Definition (e.g., FIG. 2, 210; FIG. 8. 810)

In order to identify individuals with ALS in the database to utilize in order to ultimately identify other individuals, the one or more programs define an ALS patient by utilizing information in the records related to ICD-9 and certain ALS-specific drugs, here referred to as Drug 1, Drug 2, and Drug 3. This set of patients is referred to as the "gold standard" ALS group. For example, the patient definition used for ALS consists of the ICD-9 and ICD-10 diagnosis codes along with the relevant drugs, one of which being riluzole. The program code may apply a set of definitions, which may include or exclude drugs (i.e., riluzole). In some embodiments of the present invention, the definition applied by the one or more programs may also include or exclude related conditions, along with a specific repeatability that the one or more programs identify by observing the codes.

Stage 2: Model Creation (e.g., FIG. 2, 220; FIG. 8. 820-840)

In order to identify which features or combination of features are most statistically relevant for differentiating ALS from non-ALS patients, an information-theoretical concept of mutual information was utilized to determine the differentiating features. As discussed earlier, mutual information is a measure of how much information about one set of data can be determined from another set of data. Features or their combinations with higher mutual information values are likely to be more informative for discriminating ALS from non-ALS patients.

After the program code determined the mutual information of individual features or their combinations, the program code begins feature selection. The goal of feature selection is to define the smallest subset of features that collectively contain most of the mutually shared information and thus most clearly define the characteristics of the ALS patient. As discussed above, machine learning algorithms drive the analysis of feature selection that created a model of ALS. Thus, the program code generates a model consisting of the fewest possible and simultaneously most differentiating characteristics of the ALS patients, resulting in an enhanced patient definition.

Stage 3: Prediction (e.g., FIG. 2, 230; FIG. 8. 850)

Once the program code determines a model of the characteristics of the ALS patient from the gold standard ALS patients, the program code scores the remaining population of patients in the data set by the model to find undiagnosed patients. In order to score patients, the program code computes the features for every patient in the data set not in the set of gold ALS patients. Each patient's features (or characteristics) were input to the ALS computer model and the program code produced a numerical score. This numerical score is the likelihood that the patient is an undiagnosed ALS patient. The numerical score can be used to rank patients from those who are most likely to be undiagnosed with ALS to those that are least likely to have ALS. In this case model scores were generated for over 170 million patients. The prioritized list may be used to allocate resources to better address the needs of the highest likely patients.

In an embodiment of the present invention, the training set is processed dynamically and informs and tunes the model and the data of unknown patients is continually utilized to tune the model. For example, during the building phase of the model, the output of the model with a training set input, is compared to a known label (patient with disease or not) (supervised learning). The error is used to modify the internal parameters of the model. This process continues until the error is minimized. However, once the model is built, it is then used to score the patients. For each patient (e.g., of the at least 180 million), the features are computed and fed through the model. The output of the model indicates whether the patient is a likely undiagnosed disease patient or not. (The output is binary.)

Stage 4: Validating ALS Patients

There are two approaches considered to validate that the predicted undiagnosed ALS patients actually have the condition. The first approach is to perform a field validation, where the appropriate personnel are deployed at providers to educate them on the characteristics of potential ALS patients. The providers would then call in those patients and get them tested for ALS. This process could take several months. An alternative approach is to monitor the health claims of the predicted patients over time. As the healthcare claims data is updated (monthly), new ALS patients with a definitive diagnosis indication would be flagged. In this manner the number of predicted undiagnosed patients that were validated to have the disease can be determined without engaging the sales force or medical science liaisons. In addition how far ahead in time the prediction was made before the true diagnosis can be determined.

In this example, applying the model to the remaining population of the database yielded 2,142 to 3,113 potentially undiagnosed ALS patients. The number varied depending on the specific model (generated by the program code) utilized. The information identified by the program code and incorporated in the model includes age, gender, diagnosis codes, procedures, prescriptions, provider types, and facility types. As discussed above, program code in an embodiments of the present invention may store the resultant model in a database and continually update/tune the model as the repeated application provides more intelligence.

Some embodiments of the present invention include a computer-implemented method, a computer system, and a computer program product where one or more programs in a distributed computing environment, obtain one or more machine-readable data sets related to a patient population diagnosed with a disease, from one or more databases. Based on a frequency of features in the one or more data sets, the one or more programs identify common features in the one or more data sets and weight the common features, based on frequency of occurrence in the one or more data sets, where the common features include mutual information. The one or more programs generate one or more patterns that include a portion of the common features. The one or more programs generate one or more machine learning algorithms based on the one or more patterns, the one or more machine learning algorithms to identify presence or absence of the given disease in an undiagnosed patient based on absence or presence of features comprising the one or more patterns in data related to the undiagnosed patient. The one or more programs utilize statistical sampling to compile a training set of data, wherein the training set comprises data from the one or more data sets and at least one additional data set including data related to a population without the disease, and where utilizing the statistical sampling comprises formulating and obtaining queries based on the data set and processing and responding to the queries, the processing includes, for each query: the one or more programs evaluating the query to determine one of a high or a low level of anticipated complexity of a prospective response to the query, based on the query being evaluated at a low level of anticipated complexity, the one or more programs assigning the query to a computing resource in the distributed computing environment, where the computing resource is configured to respond to low level complexity queries, and based on the query being evaluated at a high level of anticipated complexity, the one or more programs distributing the query over a group of computing resources of the distributed computing environment to maximize efficiency, where the distributing includes assigning each computing resource of the group of computing resources a portion of the query to execute in parallel with at least one other computing resource of the group of computing resources executing another portion of the query, The one or more programs tune the one or more machine learning algorithms by applying the one or more machine learning algorithms to the training set of data. The one or more programs dynamically adjust the common features including the one or more patterns to improve accuracy, such that the one or more machine learning algorithms can distinguish patient data indicating the disease from patient data that does not indicate the disease. The one or more programs determine, based on applying the one or more machine learning algorithms to data related to the undiagnosed patient, a probability, where the probability is a numerical value indicating a percentage of commonality between the data related to the undiagnosed patient and the one or more patterns.

In some embodiments of the present invention, the one or more programs generate the one or more patterns by ranking the common features based on the weighting and retaining the portion of the common features where the portion includes common features of a pre-defined weight, wherein the portion comprises the one or more patterns.

In some embodiments of the present invention, the one or more programs identify the common features based on a commonality in timestamps associated with the occurrence of the common features in the data set.

In some embodiments of the present invention, the mutual information includes features from a plurality of feature categories and wherein each pattern of the one or more patterns comprising a portion of the common features comprises features in one feature category of the plurality of feature categories.

In some embodiments of the present invention, the disease is amyotrophic lateral sclerosis and the features are selected from the group consisting of: connective tissue diseases, nervous system disorders, joint disorders, hereditary and degenerative nervous system conditions, multiple sclerosis, malaise and fatigue, and gastrointestinal disorders.

In some embodiments of the present invention, one feature category is selected from the group consisting of: diagnosis codes, procedures, drug treatments, providers, and locations.

In some embodiments of the present invention, the one or more machine learning algorithms include a linear Support Vector Machines classification algorithm.

In some embodiments of the present invention, the one or more machine learning algorithms include at least two machine learning algorithms and the tuning further includes: the one or more programs compile results of the tuning of each of the at least two machine learning algorithms and utilize ensemble learning to consolidate portions of the at least two machine learning algorithms into a single machine learning algorithm.

In some embodiments of the present invention, in tuning, the one or more programs associate, based on applying the one or more machine learning algorithms to the training set of test data, probabilities to a portion of the records in the training set of test data, wherein the probabilities reflect a likelihood of presence of the disease for each record training set of test data, and the one or more programs complete the dynamically adjusting of the common features when the probabilities are within a pre-defined accuracy threshold.

In some embodiments of the present invention, the disease is amyotrophic lateral sclerosis.

In some embodiments of the present invention, to determine the probability, the one or more programs obtain, from a computing resource, electronic medical records for the undiagnosed patient for a defined temporal period, wherein the electronic medical records comprise electronic contact information for a healthcare provider to the undiagnosed patient. The one or more programs apply the one or more machine learning algorithms to the electronic medical records. The one or more programs determine, based on the applying, if the probability is within a predetermined range. Based on determining that the probability exceeds a predetermined threshold, the one or more programs electronically alert, in real time, the healthcare provider to the undiagnosed patient of the probability. In this manner, a patient who is at a healthcare provider for an appointment, can receive time sensitive information that may lead the healthcare provider to make a diagnosis.

In some embodiments of the present invention, the one or more programs retain, in a memory resource communicatively coupled to the one or more processors, the one or more patterns. The one or more programs obtain an indication regarding accuracy of the probability. The one or more programs update the one or more patterns based on the indication.

In some embodiments of the present invention, the probability indicates a probability that the undiagnosed patient has the disease.

Figure 9:
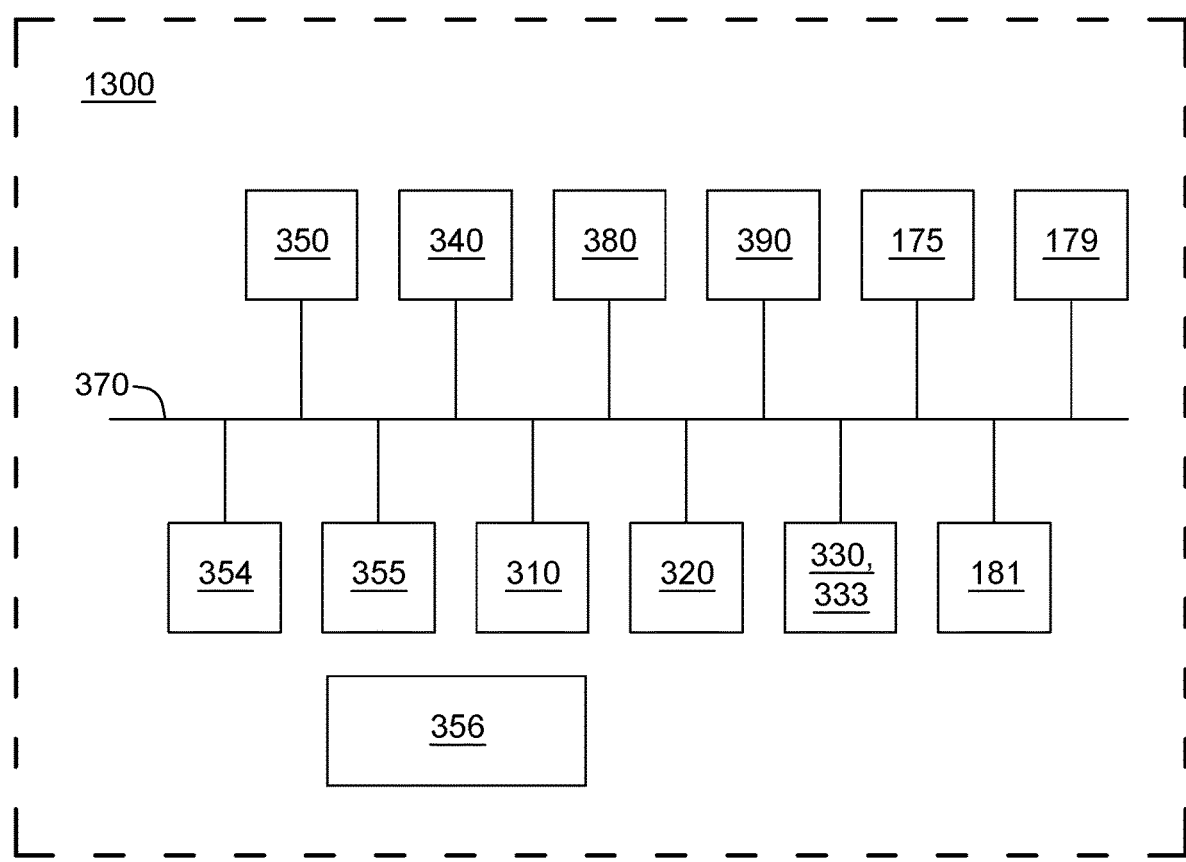
FIG. 9 depicts one embodiment of a single processor computing environment, which may comprise a node of a cloud computing environment, to incorporate and use one or more aspects of the present invention.

FIG. 9 illustrates a block diagram of a resource 1300 in computer system 110 and/or terminal 120a-120b, which is part of the technical architecture of certain embodiments of the technique. The resource 1300 may include a circuitry 370 that may in certain embodiments include a microprocessor 354. The computer system 1300 may also include a memory 355 (e.g., a volatile memory device), and storage 181. The storage 181 may include a non-volatile memory device (e.g., EPROM, ROM, PROM, RAM, DRAM, SRAM, flash, firmware, programmable logic, etc.), magnetic disk drive, optical disk drive, tape drive, etc. The storage 355 may comprise an internal storage device, an attached storage device and/or a network accessible storage device. The system 1300 may include a program logic 330 including code 333 that may be loaded into the memory 355 and executed by the microprocessor 356 or circuitry 370.

In certain embodiments, the program logic 330 including code 333 may be stored in the storage 181, or memory 355. In certain other embodiments, the program logic 333 may be implemented in the circuitry 370. Therefore, while FIG. 2 shows the program logic 333 separately from the other elements, the program logic 333 may be implemented in the memory 355 and/or the circuitry 370.

Using the processing resources of a resource 1300 to execute software, computer-readable code or instructions, does not limit where this code can be stored.

Figure 10:
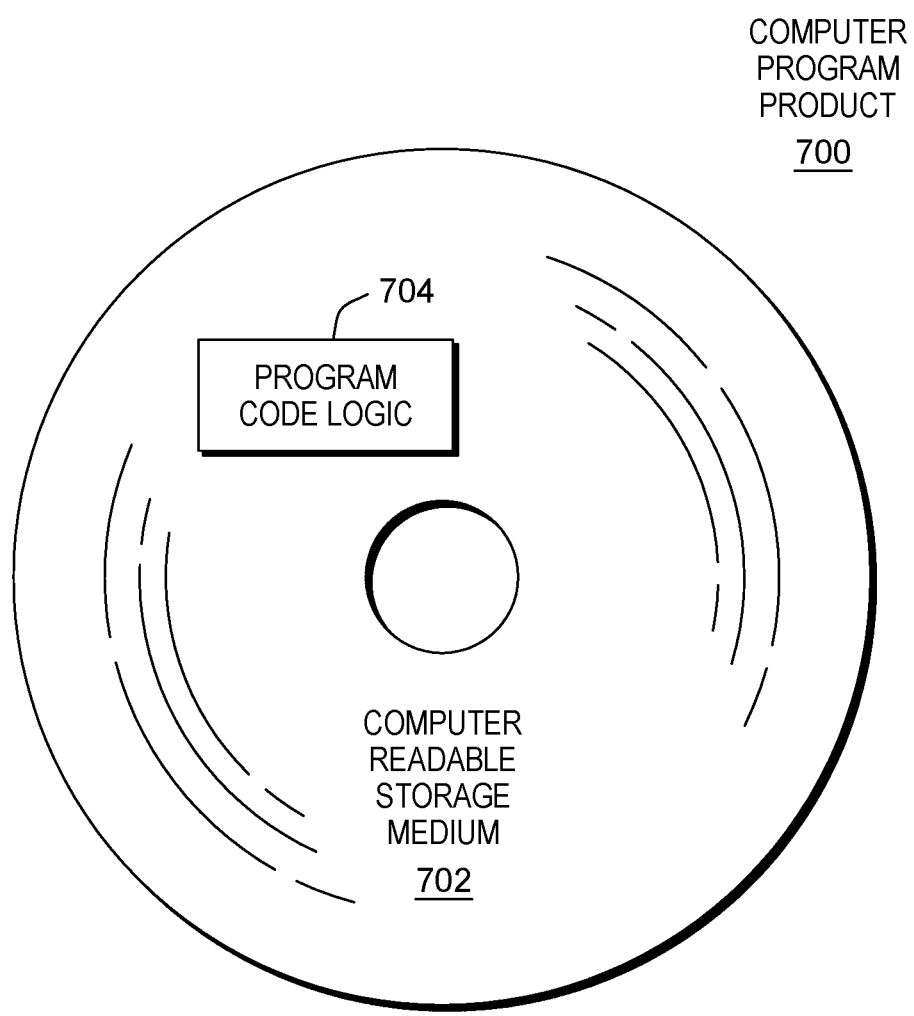
FIG. 10 depicts one embodiment of a computer program product incorporating one or more aspects of the present invention.

Referring to FIG. 10, in one example, a computer program product 700 includes, for instance, one or more non-transitory computer readable storage media 702 to store computer readable program code means or logic 704 thereon to provide and facilitate one or more aspects of the technique.

As will be appreciated by one skilled in the art, aspects of the technique may be embodied as a system, method or computer program product. Accordingly, aspects of the technique may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the technique may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Such a propagated signal may take any of a variety of forms, including, but not limited to, electro-magnetic, optical or any suitable combination thereof. A computer readable signal medium may be any computer readable medium that is not a computer readable storage medium and that can communicate, propagate, or transport a program for use by or in connection with an instruction execution system, apparatus or device.

A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the technique may be written in any combination of one or more programming languages, including an object oriented programming language, such as Java, Smalltalk, Java, Python, R-Language, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the technique are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions, also referred to as computer program code, may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In addition to the above, one or more aspects of the technique may be provided, offered, deployed, managed, serviced, etc. by a service provider who offers management of customer environments. For instance, the service provider can create, maintain, support, etc. computer code and/or a computer infrastructure that performs one or more aspects of the technique for one or more customers. In return, the service provider may receive payment from the customer under a subscription and/or fee agreement, as examples. Additionally or alternatively, the service provider may receive payment from the sale of advertising content to one or more third parties.

In one aspect of the technique, an application may be deployed for performing one or more aspects of the technique. As one example, the deploying of an application comprises providing computer infrastructure operable to perform one or more aspects of the technique.

As a further aspect of the technique, a computing infrastructure may be deployed comprising integrating computer readable code into a computing system, in which the code in combination with the computing system is capable of performing one or more aspects of the technique. As a further aspect of the technique, the system can operate in a peer to peer mode where certain system resources, including but not limited to, one or more databases, is/are shared, but the program code executable by one or more processors is loaded locally on each computer (workstation).

As yet a further aspect of the technique, a process for integrating computing infrastructure comprising integrating computer readable code into a computer system may be provided. The computer system comprises a computer readable medium, in which the computer medium comprises one or more aspects of the technique. The code in combination with the computer system is capable of performing one or more aspects of the technique.

Further, other types of computing environments can benefit from one or more aspects of the technique. As an example, an environment may include an emulator (e.g., software or other emulation mechanisms), in which a particular architecture (including, for instance, instruction execution, architected functions, such as address translation, and architected registers) or a subset thereof is emulated (e.g., on a native computer system having a processor and memory). In such an environment, one or more emulation functions of the emulator can implement one or more aspects of the technique, even though a computer executing the emulator may have a different architecture than the capabilities being emulated. As one example, in emulation mode, the specific instruction or operation being emulated is decoded, and an appropriate emulation function is built to implement the individual instruction or operation.

In an emulation environment, a host computer includes, for instance, a memory to store instructions and data; an instruction fetch unit to fetch instructions from memory and to optionally, provide local buffering for the fetched instruction; an instruction decode unit to receive the fetched instructions and to determine the type of instructions that have been fetched; and an instruction execution unit to execute the instructions. Execution may include loading data into a register from memory; storing data back to memory from a register; or performing some type of arithmetic or logical operation, as determined by the decode unit. In one example, each unit is implemented in software. For instance, the operations being performed by the units are implemented as one or more subroutines within emulator software.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

Embodiments of the present invention may be implemented in cloud computing systems. FIG. 6 may also comprise a node in this type of computing environment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the descriptions below, if any, are intended to include any structure, material, or act for performing the function in combination with other elements as specifically noted. The description of the technique has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method, comprising:

obtaining, by one or more processors in a distributed computing environment, one or more machine-readable data sets related to a patient population diagnosed with an orphan disease from one or more databases;

based on a frequency of features in the one or more data sets, identifying, by the one or more processors, common features in the one or more data sets and weighting the common features based on frequency of occurrence in the one or more data sets, wherein the common features comprise mutual information;

generating, by the one or more processors, one or more patterns comprising a portion of the common features, wherein the portion of the features comprises a smallest number of the common features that is a largest number of differentiating characteristics of the patient population diagnosed with the orphan disease, wherein the portion of the common features is identified based on comparing members of a general population, wherein the general population comprises the patient population and an additional population, wherein the patient population comprises patients diagnosed with the orphan disease and the additional population comprises patients not diagnosed with the orphan disease, wherein a portion of the patient population diagnosed with the medical condition has the differentiating characteristics, and wherein the portion comprises fewer patients than the patients comprising the patient population;

generating, by the one or more processors, one or more machine learning algorithms based on the one or more patterns, the one or more machine learning algorithms to identify presence or absence of the given orphan disease in an undiagnosed patient based on absence or presence of features comprising the one or more patterns in data related to the undiagnosed patient;

utilizing, by the one or more processors, statistical sampling to compile a training set of data, wherein the training set comprises data from the one or more data sets related to the patient population diagnosed with the orphan disease and at least one additional data set comprising data related to a population without the orphan disease, wherein the statistical sampling comprises proportionally selecting representative electronic medical records from two data sources, the two data sources comprising: one or more data sets related to the patient population diagnosed with the orphan disease, and at least one additional data set comprising data related to the population without the orphan disease, wherein the representative electronic medical records from the data from the one or more data sets related to the patient population diagnosed with the orphan disease comprise a target population, and wherein the representative electronic medical records from the at least one additional data set comprising data related to the population without the orphan disease comprise a control population, and wherein utilizing the statistical sampling comprises formulating and obtaining queries based on the data set and processing and responding to the queries, the processing comprising, for each query:
  evaluating, by the one or more processors, the query to determine if a prospective response to the query is a single value pulled from a single data set;
  based on determining that the prospective response to the query is the single value pulled from the single data set assigning, by the one or more processors, the query to a given computing resource in the distributed computing environment; and
  based on determining that the prospective response to the query is not the single value pulled from the single data set, distributing, by the one or more processors, the query over a group of computing resources of the distributed computing environment to maximize efficiency, wherein the distributing comprises assigning each computing resource of the group of computing resources a portion of the query to execute in parallel with at least one other computing resource of the group of computing resources executing another portion of the query;
tuning, by the one or more processors, the one or more machine learning algorithms by applying the one or more machine learning algorithms to the training set of data;
dynamically adjusting, by the one or more processors, the common features comprising the one or more patterns to improve accuracy such that the one or more machine learning algorithms can distinguish patient data indicating the orphan disease from patient data that does not indicate the orphan disease, wherein the dynamically adjusting narrows the target population; and
determining, by the one or more processors, based on applying the one or more machine learning algorithms to data related to the undiagnosed patient, a probability, wherein the probability is a numerical value indicating a percentage of commonality between the data related to the undiagnosed patient and the one or more patterns, wherein the probability indicates a probability that the undiagnosed patient will be diagnosed with the orphan disease in the future.

2. The method of claim 1, wherein the generating the one or more patterns comprises:
  ranking, by the one or more processors, the common features based on the weighting; and
  retaining, by the one or more processors, the portion of the common features wherein the portion comprises common features of a pre-defined weight, wherein the portion comprises the one or more patterns.

3. The method of claim 1, wherein the identifying of the common features is also based on a commonality in timestamps associated with the occurrence of the common features in the data set.

4. The method of claim 1, wherein the mutual information comprises features from a plurality of feature categories and wherein each pattern of the one or more patterns comprising a portion of the common features comprises features in one feature category of the plurality of feature categories.

5. The method of claim 4, wherein the orphan disease is amyotrophic lateral sclerosis and the features are selected from the group consisting of: connective tissue diseases, nervous system disorders, joint disorders, hereditary and degenerative nervous system conditions, multiple sclerosis, malaise and fatigue, and gastrointestinal disorders.

6. The method of claim 4, wherein the one feature category is selected from the group consisting of: diagnosis codes, procedures, drug treatments, providers, and locations.

7. The method of claim 1, wherein the one or more machine learning algorithms comprise a linear Support Vector Machines classification algorithm.

8. The method of claim 1, wherein the one or more machine learning algorithms comprise at least two machine learning algorithms and wherein the tuning further comprises:
  compiling results of the tuning of each of the at least two machine learning algorithms and utilizing ensemble learning to consolidate portions of the at least two machine learning algorithms into a single machine learning algorithm.

9. The method of claim 1, the tuning further comprising:
  associating, by the one or more processors, based on applying the one or more machine learning algorithms to the training set of test data, probabilities to a portion of the records in the training set of test data, wherein the probabilities reflect a likelihood of presence of the orphan disease for each record training set of test data; and
  completing the dynamically adjusting of the common features when the probabilities are within a pre-defined accuracy threshold.

10. The method of claim 1, wherein the orphan disease is amyotrophic lateral sclerosis.

11. The method of claim 1, wherein the determining the probability:
  obtaining, by the one or more processors, from a computing resource, electronic medical records for the undiagnosed patient for a defined temporal period, wherein the electronic medical records comprise electronic contact information for a healthcare provider to the undiagnosed patient;
  applying, by the one or more processors, the one or more machine learning algorithms to the electronic medical records;
  determining, by the one or more processors, based on the applying, if the probability is within a predetermined range; and
  based on determining that the probability exceeds a predetermined threshold, electronically alerting, in real time, the healthcare provider to the undiagnosed patient of the probability.

12. The method of claim 11, further comprising:
  retaining, by the one or more processors, in a memory resource communicatively coupled to the one or more processors, the one or more patterns;
  obtaining, by the one or more processors, an indication regarding accuracy of the probability; and
  updating, by the one or more processors, the one or more patterns based on the indication.

13. The method of claim 11, wherein the probability indicates a probability that the undiagnosed patient has the orphan disease.

14. A computer program product comprising:
a non-transitory computer readable storage medium readable by one or more processors in a distributed computing environment, and storing instructions for execution by the one or more processors for performing a method comprising:
- obtaining, by the one or more processors in a distributed computing environment, one or more machine-readable data sets related to a patient population diagnosed with an orphan disease from one or more databases;
- based on a frequency of features in the one or more data sets, identifying, by the one or more processors, common features in the one or more data sets and weighting the common features based on frequency of occurrence in the one or more data sets, wherein the common features comprise mutual information;
- generating, by the one or more processors, one or more patterns comprising a portion of the common features, wherein the portion of the features comprises a smallest number of the common features that is a largest number of differentiating characteristics of the patient population diagnosed with the orphan disease, wherein the portion of the common features is identified based on comparing members of a general population, wherein the general population comprises the patient population and an additional population, wherein the patient population comprises patients diagnosed with the orphan disease and the additional population comprises patients not diagnosed with the orphan disease, wherein a portion of the patient population diagnosed with the medical condition has the differentiating characteristics, and wherein the portion comprises fewer patients than the patients comprising the patient population;
- generating, by the one or more processors, one or more machine learning algorithms based on the one or more patterns, the one or more machine learning algorithms to identify presence or absence of the given orphan disease in an undiagnosed patient based on absence or presence of features comprising the one or more patterns in data related to the undiagnosed patient;
- utilizing, by the one or more processors, statistical sampling to compile a training set of data, wherein the training set comprises data from the one or more data sets related to the patient population diagnosed with the orphan disease and at least one additional data set comprising data related to a population without the orphan disease, wherein the statistical sampling comprises proportionally selecting representative electronic medical records from two data sources, the two data sources comprising: one or more data sets related to the patient population diagnosed with the orphan disease, and at least one additional data set comprising data related to the population without the orphan disease, wherein the representative electronic medical records from the data from the one or more data sets related to the patient population diagnosed with the orphan disease comprise a target population, and wherein the representative electronic medical records from the at least one additional data set comprising data related to the population without the orphan disease comprise a control population, and wherein utilizing the statistical sampling comprises formulating and obtaining queries based on the data set and processing and responding to the queries, the processing comprising, for each query:
  - evaluating, by the one or more processors, the query to determine if a prospective response to the query is a single value pulled from a single data set;
  - based on determining that the prospective response to the query is the single value pulled from the single data set, assigning, by the one or more processors, the query to a given computing resource in the distributed computing environment; and
  - based on determining that the prospective response to the query is not the single value pulled from the single data set, distributing, by the one or more processors, the query over a group of computing resources of the distributed computing environment to maximize efficiency, wherein the distributing comprises assigning each computing resource of the group of computing resources a portion of the query to execute in parallel with at least one other computing resource of the group of computing resources executing another portion of the query;
- tuning, by the one or more processors, the one or more machine learning algorithms by applying the one or more machine learning algorithms to the training set of data;
- dynamically adjusting, by the one or more processors, the common features comprising the one or more patterns to improve accuracy such that the one or more machine learning algorithms can distinguish patient data indicating the orphan disease from patient data that does not indicate the orphan disease, wherein the dynamically adjusting narrows the target population; and
- determining, by the one or more processors, based on applying the one or more machine learning algorithms to data related to the undiagnosed patient, a probability, wherein the probability is a numerical value indicating a percentage of commonality between the data related to the undiagnosed patient and the one or more patterns, wherein the probability indicates a probability that the undiagnosed patient will be diagnosed with the orphan disease in the future.

15. The computer program product of claim 14, wherein the generating the one or more patterns comprises:
- ranking, by the one or more processors, the common features based on the weighting; and
- retaining, by the one or more processors, the portion of the common features wherein the portion comprises common features of a pre-defined weight, wherein the portion comprises the one or more patterns.

16. The computer program product of claim 14, wherein the mutual information comprises features from a plurality of feature categories and wherein each pattern of the one or more patterns comprising a portion of the common features comprises features in one feature category of the plurality of feature categories.

17. The computer program product of claim 14, wherein the one feature category is selected from the group consisting of: diagnosis codes, procedures, drug treatments, and locations.

18. The computer program product of claim 14, wherein the machine learning algorithm comprises a linear Support Vector Machines classification algorithm.

19. A system comprising:
one or more memory;
one or more processors in communication with the memory; and
program instructions executable by the one or more processors in a distributed computed environment via the one or more memory to perform a method, the method comprising:
  obtaining, by the one or more processors in a distributed computing environment, one or more machine-readable data sets related to a patient population diagnosed with an orphan disease from one or more databases;
  based on a frequency of features in the one or more data sets, identifying, by the one or more processors, common features in the one or more data sets and weighting the common features based on frequency of occurrence in the one or more data sets, wherein the common features comprise mutual information;
  generating, by the one or more processors, one or more patterns comprising a portion of the common features, wherein the portion of the features comprises a smallest number of the common features that is a largest number of differentiating characteristics of the patient population diagnosed with the orphan disease, wherein the portion of the common features is identified based on comparing members of a general population, wherein the general population comprises the patient population and an additional population, wherein the patient population comprises patients diagnosed with the orphan disease and the additional population comprises patients not diagnosed with the orphan disease, wherein a portion of the patient population diagnosed with the medical condition has the differentiating characteristics, and wherein the portion comprises fewer patients than the patients comprising the patient population;
  generating, by the one or more processors, one or more machine learning algorithms based on the one or more patterns, the one or more machine learning algorithms to identify presence or absence of the given orphan disease in an undiagnosed patient based on absence or presence of features comprising the one or more patterns in data related to the undiagnosed patient;
  utilizing, by the one or more processors, statistical sampling to compile a training set of data, wherein the training set comprises data from the one or more data sets related to the patient population diagnosed with the orphan disease and at least one additional data set comprising data related to a population without the orphan disease, wherein the statistical sampling comprises proportionally selecting representative electronic medical records from two data sources, the two data sources comprising: one or more data sets related to the patient population diagnosed with the orphan disease, and at least one additional data set comprising data related to the population without the orphan disease, wherein the representative electronic medical records from the data from the one or more data sets related to the patient population diagnosed with the orphan disease comprise a target population, and wherein the representative electronic medical records from the at least one additional data set comprising data related to the population without the orphan disease comprise a control population, and wherein utilizing the statistical sampling comprises formulating and obtaining queries based on the data set and processing and responding to the queries, the processing comprising, for each query:
    evaluating, by the one or more processors, the query to determine if a prospective response to the query is a single value pulled from a single data set;
    based on determining that the prospective response to the query is the single value pulled from the single data set, assigning, by the one or more processors, the query to a given computing resource in the distributed computing environment; and
    based on determining that the prospective response to the query is not the single value pulled from the single data set, distributing, by the one or more processors, the query over a group of computing resources of the distributed computing environment to maximize efficiency, wherein the distributing comprises assigning each computing resource of the group of computing resources a portion of the query to execute in parallel with at least one other computing resource of the group of computing resources executing another portion of the query;
  tuning, by the one or more processors, the one or more machine learning algorithms by applying the one or more machine learning algorithms to the training set of data;
  dynamically adjusting, by the one or more processors, the common features comprising the one or more patterns to improve accuracy such that the one or more machine learning algorithms can distinguish patient data indicating the orphan disease from patient data that does not indicate the orphan disease, wherein the dynamically adjusting narrows the target population; and
  determining, by the one or more processors, based on applying the one or more machine learning algorithms to data related to the undiagnosed patient, a probability, wherein the probability is a numerical value indicating a percentage of commonality between the data related to the undiagnosed patient and the one or more patterns, wherein the probability indicates a probability that the undiagnosed patient will be diagnosed with the orphan disease in the future.

* * * * *